(12) United States Patent
Ishikawa et al.

(10) Patent No.: US 12,318,127 B2
(45) Date of Patent: Jun. 3, 2025

(54) ENDOSCOPE TREATMENT TOOL

(71) Applicant: FUJIFILM Corporation, Tokyo (JP)

(72) Inventors: Ryo Ishikawa, Kanagawa (JP); Jun Sato, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 638 days.

(21) Appl. No.: 17/128,180

(22) Filed: Dec. 20, 2020

(65) Prior Publication Data

US 2021/0106375 A1 Apr. 15, 2021

Related U.S. Application Data

(63) Continuation of application No. PCT/JP2019/024527, filed on Jun. 20, 2019.

(30) Foreign Application Priority Data

Jul. 23, 2018 (JP) .................................. 2018-137453

(51) Int. Cl.
*A61B 18/14* (2006.01)
*A61B 18/00* (2006.01)
*A61B 90/00* (2016.01)

(52) U.S. Cl.
CPC .............. *A61B 18/14* (2013.01); *A61B 90/03* (2016.02); *A61B 2018/00172* (2013.01);
(Continued)

(58) Field of Classification Search
CPC ................... A61B 18/14; A61B 90/03; A61B 2018/00172; A61B 2018/00482;
(Continued)

(56) References Cited

U.S. PATENT DOCUMENTS 6,770,070 B1 * 8/2004 Balbierz .......... A61B 17/00491
606/41
6,827,718 B2 12/2004 Hutchins et al.
(Continued)

FOREIGN PATENT DOCUMENTS

CN      102688082      9/2012
JP      2005511195     4/2005
(Continued)

OTHER PUBLICATIONS

"International Search Report (Form PCT/ISA/210) of PCT/JP2019/024527," mailed on Aug. 27, 2019, with English translation thereof, pp. 1-5.
(Continued)

*Primary Examiner* — Joseph A Stoklosa
*Assistant Examiner* — Annie L Shoulders
(74) *Attorney, Agent, or Firm* — JCIPRNET

(57) ABSTRACT

Provided is an endoscope treatment tool of which the usability is favorable regardless of which of a syringe and a water supply tube is used by being connected to a water injection connector. A connector body (18) is connected to an operation part body (22) such that the connector body (18) is rotatable around a rotation axis (28). The operation part body (22) includes a rotation stopper (60) that restricts rotation of the connector body (18). The connector body (18) includes an abutting surface (62) that abuts the rotation stopper (60). The connector body (18) is capable of transitioning between a rotation restricted state, in which the abutting surface (62) abuts the rotation stopper (60) such that rotation of the connector body (18) in one direction is restricted, and a rotation allowed state, in which the abutting surface (62) abutting the rotation stopper (60) is released and rotation of the connector body (18) in both directions is
(Continued)

allowed, by rotating with respect to the operation part body (22).

18 Claims, 16 Drawing Sheets

(52) U.S. Cl.
CPC ............. *A61B 2018/00482* (2013.01); *A61B 2018/144* (2013.01); *A61B 2018/1475* (2013.01); *A61B 2090/035* (2016.02); *A61B 2218/002* (2013.01)

(58) Field of Classification Search
CPC ...... A61B 2018/144; A61B 2018/1475; A61B 2090/035
See application file for complete search history.

(56) References Cited

U.S. PATENT DOCUMENTS

| | | | |
|---|---|---|---|
| 7,635,363 | B2 | 12/2009 | Hutchins et al. |
| 8,231,621 | B2 | 7/2012 | Hutchins et al. |
| 8,579,895 | B2 | 11/2013 | Hutchins et al. |
| 9,352,124 | B2 | 5/2016 | Hutchins et al. |
| 2007/0100337 | A1 | 5/2007 | Kawahara et al. |
| 2008/0027429 | A1 | 1/2008 | Oyatsu |
| 2012/0296327 | A1* | 11/2012 | Hutchins ............ A61B 18/1492 606/33 |
| 2016/0256217 | A1 | 9/2016 | Hutchins et al. |
| 2017/0007101 | A1* | 1/2017 | Dejima .............. A61B 17/3462 |
| 2017/0119451 | A1 | 5/2017 | Komiya et al. |
| 2018/0117280 | A1* | 5/2018 | Chu ....................... A61B 1/307 |
| 2018/0368869 | A1* | 12/2018 | Kuriki ................ A61B 18/1442 |
| 2019/0090937 | A1 | 3/2019 | Kano |

FOREIGN PATENT DOCUMENTS

| | | |
|---|---|---|
| JP | 2007117532 | 5/2007 |
| JP | 2008029667 | 2/2008 |
| JP | 2012075657 | 4/2012 |
| WO | 2016009702 | 1/2016 |
| WO | 2017203636 | 11/2017 |

OTHER PUBLICATIONS

"International Preliminary Report on Patentability (Form PCT/IPEA/409) of PCT/JP2019/024527," completed on Jan. 16, 2020, with English translation thereof, pp. 1-7.

"Search Report of Europe Counterpart Application", issued on Nov. 30, 2021, pp. 1-8.

"Office Action of China Counterpart Application", issued on Dec. 1, 2023, with English translation thereof, p. 1-p. 15.

* cited by examiner

ENDOSCOPE TREATMENT TOOL

CROSS-REFERENCE TO RELATED APPLICATIONS

The present application is a Continuation of PCT International Application No. PCT/JP2019/024527 filed on Jun. 20, 2019 claiming priority under 35 U.S.C. § 119(a) to Japanese Patent Application No. 2018-137453 filed on Jul. 23, 2018. Each of the above applications is hereby expressly incorporated by reference, in its entirety, into the present application.

BACKGROUND OF THE INVENTION

1. Field of the Invention

The present invention relates to an endoscope treatment tool, and particularly to an endoscope treatment tool that is inserted into a treatment tool insertion channel of an endoscope and performs treatment such as incision or peeling of a lesioned mucous membrane part.

2. Description of the Related Art

As an example of treatment in which an endoscope is used, endoscopic submucosal dissection (ESD) is known. ESD is treatment in which a lesioned mucous membrane is excised by means of an endoscope treatment tool in a case where a lesion part such as a tumor is found at a mucous membrane part of a body cavity inner wall of an esophagus, a stomach, a duodenum, a large intestine, and the like during an endoscopy.

As the endoscope treatment tool used in ESD, for example, a high-frequency treatment tool disclosed in JP2008-029667A is known.

The high-frequency treatment tool in JP2008-029667A includes a connector body (connection pipe) between a flexible sheath having a distal end with a high-frequency knife and an operation part body (operation unit) consisting of a body shaft and a slider and the connector body is provided with a water injection connector (fluid connection portion). In the case of the high-frequency treatment tool, a syringe, a water supply tube (pipe), or the like can be connected to the water injection connector.

Note that, JP2005-511195A discloses a catheter device removing a gallstone although the catheter device is not an endoscope treatment tool for ESD. In the case of the catheter device, a handle is rotatably provided with respect to a catheter hub assembly and meshing type detents are engaged with each other such that rotation of the handle is restricted and the position of an endoscope tool is maintained. In addition, in the catheter device, the handle is configured to be able to rotate with respect to the catheter hub assembly with a frictional force.

SUMMARY OF THE INVENTION

Although the connector body is connected to the operation part body in the high-frequency treatment tool disclosed in JP2008-029667A, it is not clear whether the connector body is connected to the operation part body such that the connector body cannot rotate or the connector body is connected to the operation part body such that the connector body can rotate.

In the case of a configuration in which the connector body is connected to the operation part body such that the connector body cannot rotate, it is possible to easily connect a syringe to the water injection connector and a state where the syringe faces a predetermined direction is maintained even in the case of operation of the high-frequency treatment tool. Therefore, it becomes easy to operate the high-frequency treatment tool even in the case of connection and operation of the syringe. However, in a case where the water supply tube is used by being connected to the water injection connector, the water supply tube may hinder the operation of the endoscope treatment tool in a case where there is a change in positional relationship between the endoscope treatment tool and the water supply tube, which is likely to cause a decrease in operability. Note that, the catheter device disclosed in JP2005-511195A also has the same problem since the catheter hub assembly and the handle are attached with a frictional force.

Meanwhile, in the case of a configuration in which the connector body is connected to the operation part body such that the connector body can rotate, even in a case where there is a change in positional relationship between the endoscope treatment tool and the water supply tube in the case of connection of the water supply tube, the change can be absorbed with rotation of the connector body and thus the operability is favorable. However, in the case of such a configuration, the connector body is rotated and the syringe hangs down due to the weight of the syringe in the case of connection of the syringe and the syringe swings with the high-frequency treatment tool operated, which causes a decrease in operability.

In view of circumstances described above, an object of the present invention is to provide an endoscope treatment tool of which the usability is favorable regardless of which of a syringe and a water supply tube is used by being connected to a water injection connector.

In order to solve the object of the present invention, an endoscope treatment tool according to an aspect of the present invention comprises a flexible sheath, a wire that is inserted into the sheath, a treatment unit that is provided at a distal end of the wire, a connector body having a tubular shape to which a proximal end of the sheath is connected, a water injection connector that is provided at the connector body, and an operation part body that is connected to a proximal end of the connector body and moves the wire forward and backward in an axial direction of the sheath such that the treatment unit projects and retracts from a distal end of the sheath. The connector body is connected to the operation part body such that the connector body is rotatable around a rotation axis, the operation part body includes a rotation stopper, the connector body includes an abutting surface, and the connector body is capable of transitioning between a rotation restricted state, in which the abutting surface abuts the rotation stopper such that rotation of the connector body in one direction is restricted, and a rotation allowed state, in which the abutting surface abutting the rotation stopper is released and rotation of the connector body in both directions is allowed, by rotating with respect to the operation part body.

In order to solve the object of the present invention, an endoscope treatment tool according to another aspect of the present invention comprises a flexible sheath, a wire that is inserted into the sheath, a treatment unit that is provided at a distal end of the wire, a connector body having a tubular shape to which a proximal end of the sheath is connected, a water injection connector that is provided at the connector body, and an operation part body that is connected to a proximal end of the connector body and moves the wire forward and backward in an axial direction of the sheath such that the treatment unit projects and retracts from a distal end of the sheath. The connector body is connected to the operation part body such that the connector body rotatable around a rotation axis, the operation part body includes a rotation stopper, the connector body includes an abutting surface, and the rotation stopper is provided at a position overlapping a portion of a rotation trajectory of the abutting surface as seen in a direction along the rotation axis and is configured to restrict rotation of the connector body in one direction with the abutting surface abutting the rotation stopper.

In the aspect of the present invention, in a state where the rotation axis is disposed along a first direction which is one of horizontal directions, when it is assumed that a reference angle is a rotation angle of the connector body in a case where a central axis of the water injection connector is directed to a second direction which is one of the horizontal directions orthogonal to the first direction, a difference between the reference angle and a rotation angle of the connector body is restricted is within 45 degrees, in a case where the abutting surface abuts on the rotation stopper to restrict the rotation of the connector body in the one direction.

In the aspect of the present invention, the connector body preferably includes a first peripheral surface extending along a circumferential direction around the rotation axis, the operation part body preferably includes a second peripheral surface extending along the circumferential direction around the rotation axis, the abutting surface is preferably provided on the first peripheral surface, and the rotation stopper is preferably provided on the second peripheral surface.

In the aspect of the present invention, the second peripheral surface is preferably provided with a sliding contact surface having a convex shape and the connector body is preferably configured to be rotate while abutting the sliding contact surface.

In the aspect of the present invention, the rotation stopper is preferably configured such that a position of the rotation stopper in a circumferential direction around the rotation axis in the operation part body is changeable.

In the aspect of the present invention, the central axis of the water injection connector is preferably orthogonal to the rotation axis.

In the aspect of the present invention, the connector body preferably includes an engaged portion and the operation part body preferably includes a movable engaging body that is capable of operating between a rotation locked state in which the movable engaging body engages with the engaged portion and the connector body is locked so that the connector body is not rotatable and a rotation unlocked state in which the movable engaging body is disengaged from the engaged portion so that the connector body is rotatable.

In the aspect of the present invention, the movable engaging body is preferably a slide switch that is capable of sliding in an axial direction along the rotation axis.

In the aspect of the present invention, the movable engaging body is preferably a rocking switch that is capable of rocking around a direction orthogonal to an axial direction along the rotation axis.

In the aspect of the present invention, the operation part body preferably includes a body shaft portion to which the connector body is rotatably connected and that extends in a direction along the rotation axis, a slider that is provided to be movable along the body shaft portion and to which a proximal end portion of the wire is connected, and an electrical connector that is provided in the slider and is electrically connected to the proximal end portion of the wire and the operation part body is preferably capable of energizing the treatment unit.

According to the aspects of the present invention, usability is favorable regardless of which of a syringe and a water supply tube is used by being connected to a water injection connector.

DESCRIPTION OF THE PREFERRED EMBODIMENTS

Hereinafter, a preferred embodiment of an endoscope treatment tool according to an embodiment of the present invention will be described with reference to the accompanying drawings.

In the following embodiment, as an example of an endoscope treatment tool, a high-frequency treatment tool used in ESD will be described. However, the endoscope treatment tool according to the embodiment of the present invention can also be applied to an endoscope treatment tool that performs treatment other than this type of treatment.

Figure 1:
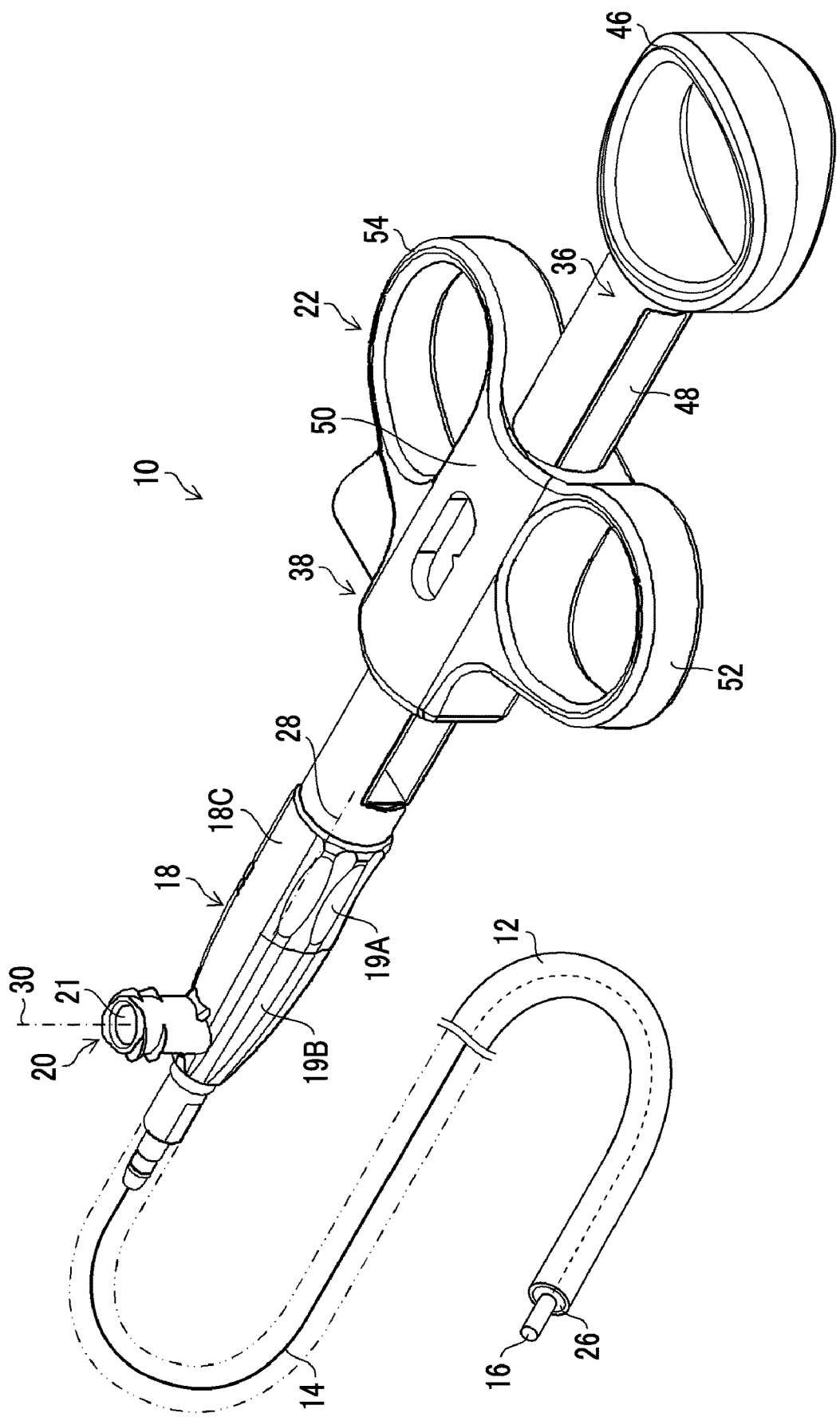
FIG. 1 is a perspective view of a high-frequency treatment tool according to a first embodiment as seen in one direction.
Figure 2:
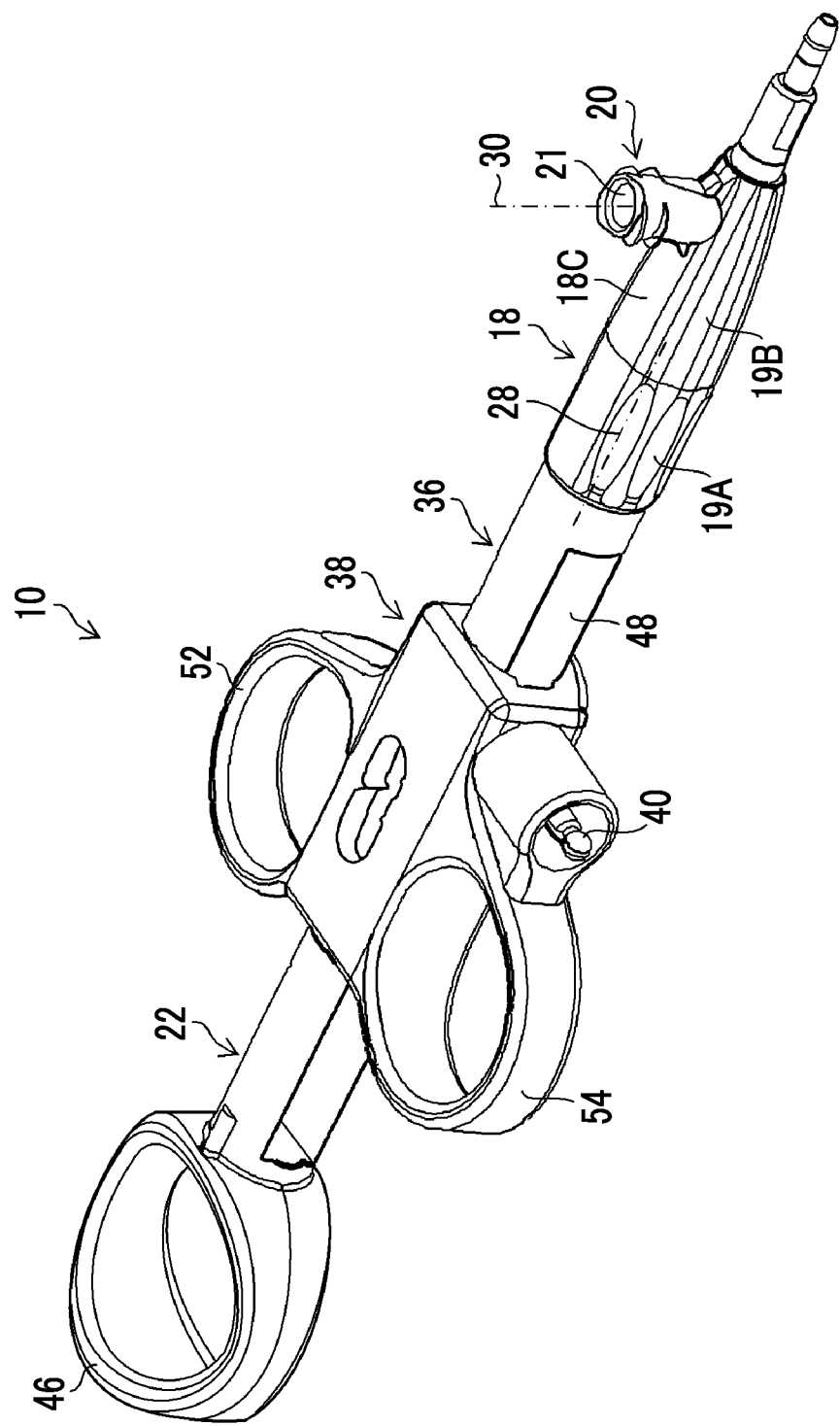
FIG. 2 is a perspective view showing the high-frequency treatment tool as seen in the other direction.
Figure 3:
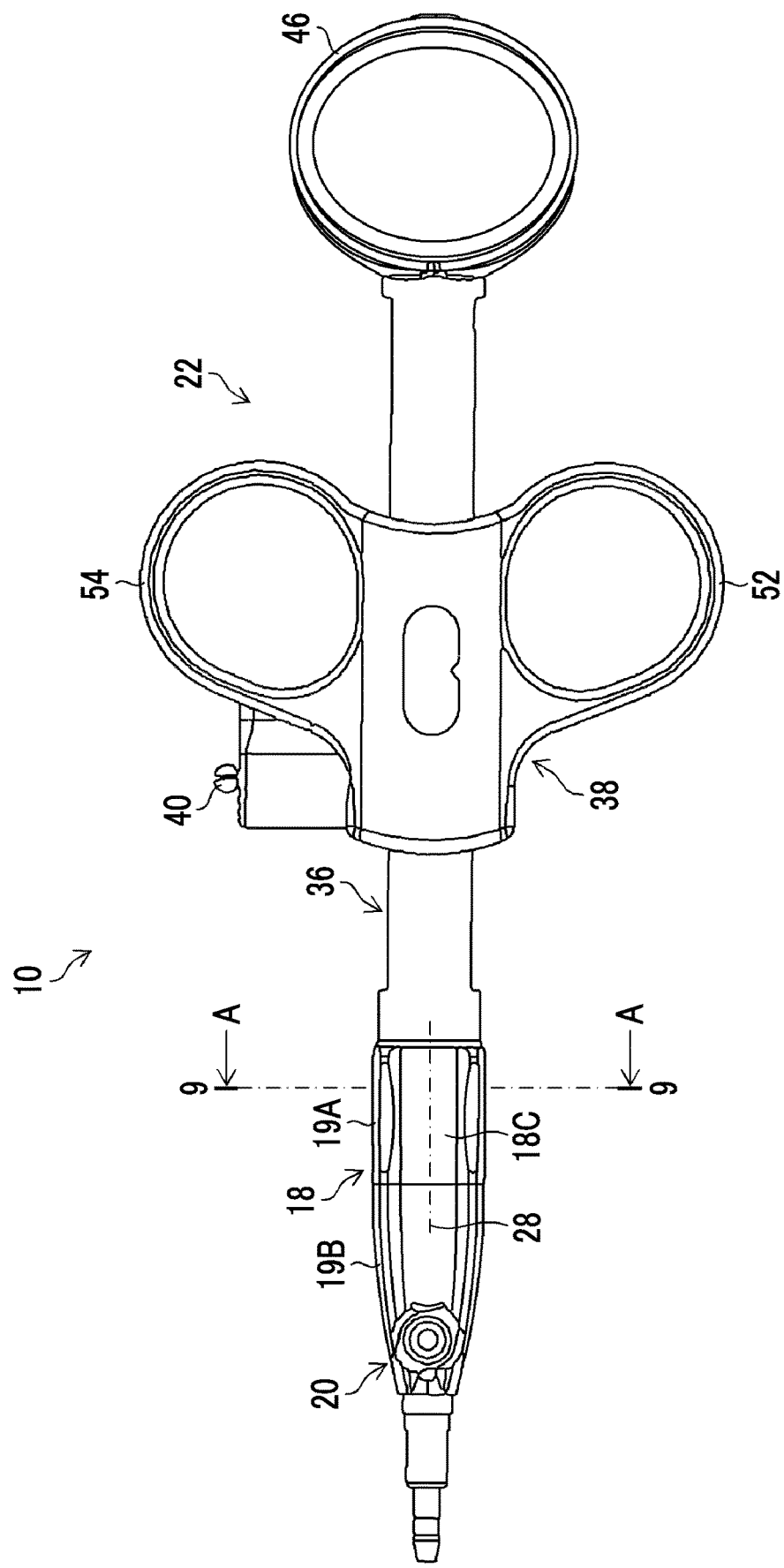
FIG. 3 is a plan view of the high-frequency treatment tool.
Figure 4:
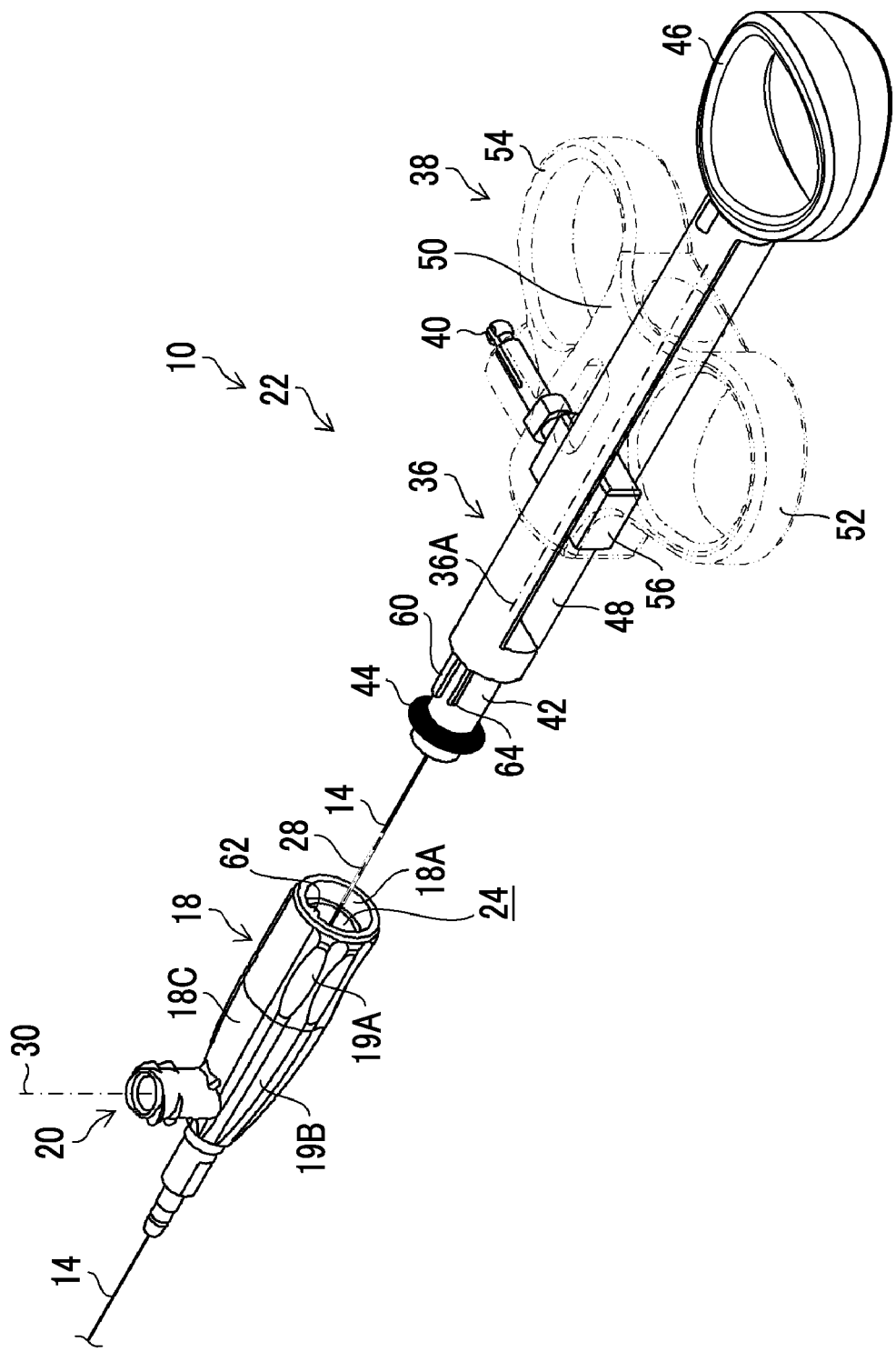
FIG. 4 is an assembly perspective view in which constituent members of the high-frequency treatment tool are shown separately.

FIG. 1 is an overall perspective view showing an example of a high-frequency treatment tool 10 according to a first embodiment and is a perspective view showing the high-frequency treatment tool 10 as seen in one direction. On the other hand, FIG. 2 is a perspective view showing the high-frequency treatment tool 10 as seen in the other direction. In addition, FIG. 3 is a plan view of the high-frequency treatment tool 10 and FIG. 4 is an assembly perspective view of the high-frequency treatment tool 10 in which constituent members of the high-frequency treatment tool 10 are shown separately.

As shown in FIG. 1, the high-frequency treatment tool 10 comprises a flexible sheath 12, a wire 14 that is inserted into the sheath 12, a high-frequency knife 16 that is provided at a distal end of the wire 14, a connector body 18, a water injection connector 20 that is provided at the connector body 18, and an operation part body 22.

The sheath 12 is composed of an insulating member, has a long length, and is inserted into a treatment tool insertion channel of an endoscope (not shown) in the case of ESD treatment. Note that, the sheath 12 is shown only in FIG. 1 and the sheath 12 is not shown in FIG. 2 and the subsequent drawings.

The distal end of the wire 14 is provided with the high-frequency knife 16, which is an example of a treatment unit. In addition, a proximal end of the wire 14 is inserted into an internal space 24 (refer to FIG. 4) of the connector body 18 and is connected to a core 56 (refer to FIG. 4) of the operation part body 22. The wire 14 in the embodiment is, for example, configured by covering a conductive wire (not shown) with an insulating coat (not shown).

Figure 5:
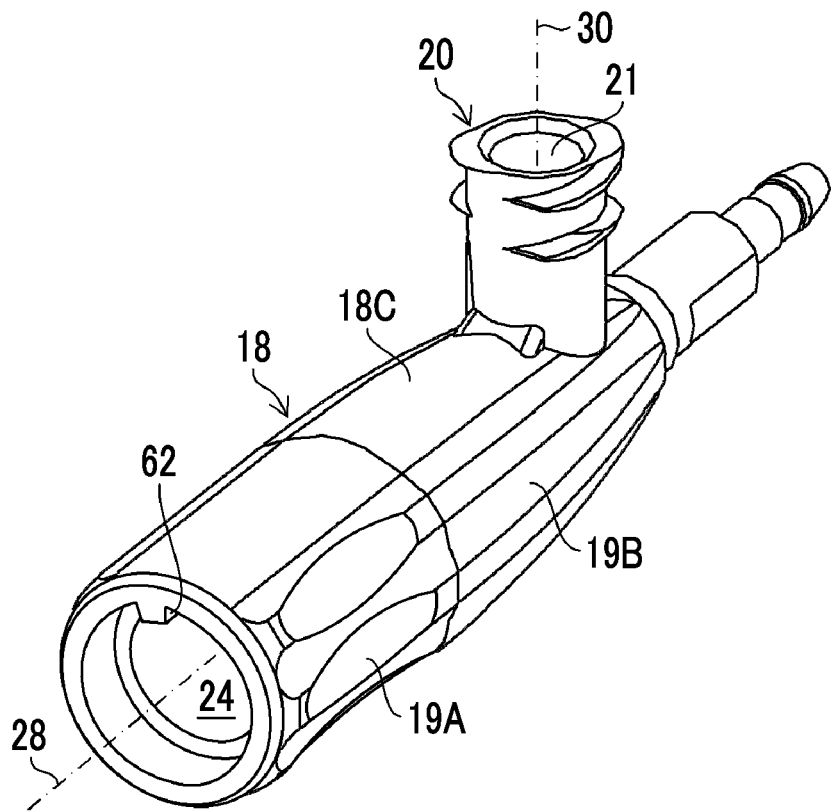
FIG. 5 is an enlarged perspective view of a connector body.
Figure 6:
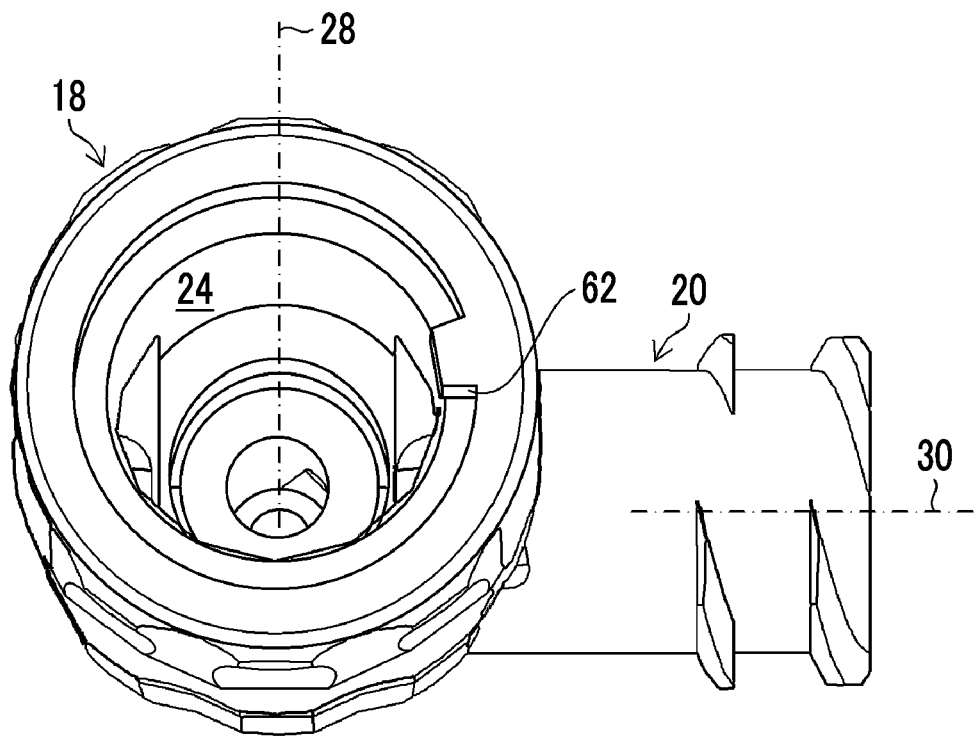
FIG. 6 is a perspective view showing an internal space of the connector body.

FIG. 5 is an enlarged perspective view of the connector body 18. FIG. 6 is a perspective view particularly showing the internal space 24 of the connector body 18. As shown in FIGS. 1 to 6, the connector body 18 is a tubular member that connects a proximal end of the sheath 12 and a distal end of the operation part body 22 to each other and is connected to the operation part body 22 such that the connector body 18 can rotate around a rotation axis 28.

In addition, an outer peripheral surface 18C of the connector body 18 includes a finger hook portion 19A and a slip prevention portion 19B. The finger hook portion 19A is provided on the operation part body 22 side and the slip prevention portion 19B is provided on the sheath 12 side. In addition, on the finger hook portion 19A, a plurality of curved surfaces having an approximately elliptical shape, of which the diameter is long in a direction along the rotation axis 28, are formed along a circumferential direction of the outer peripheral surface 18C. On the slip prevention portion 19B, a plurality of grooves extending along the direction along the rotation axis 28 are formed along the circumferential direction of the outer peripheral surface 18C.

As shown in FIGS. 5 and 6, at the connector body 18, the water injection connector 20 is formed to protrude laterally. The water injection connector 20 is configured to have a tubular shape and a water injection path 21 is formed therein. One end of the water injection path 21 communicates with the internal space 24 of the connector body 18. In addition, the other end of the water injection path 21 is open at an end portion of the water injection connector 20. The water injection connector 20 is connected to the connector body 18 in such a direction that a central axis 30 of the water injection connector 20 is orthogonal to the rotation axis 28 of the connector body 18, for example. Since the water injection connector 20 is connected to the connector body 18 in such a direction, a syringe 32 (refer to FIG. 7) or a water supply tube 34 (refer to FIG. 8), which will be described later, does not hinder an operator operating the high-frequency treatment tool 10 in the case of operation of the high-frequency treatment tool 10 and thus the operator can concentrate on the operation of the high-frequency treatment tool 10. Note that, the endoscope treatment tool according to the embodiment of the present invention is not limited to the above-described connection method and a connection method in which the central axis 30 is inclined with respect to the rotation axis 28 may also be adopted.

Figure 7:
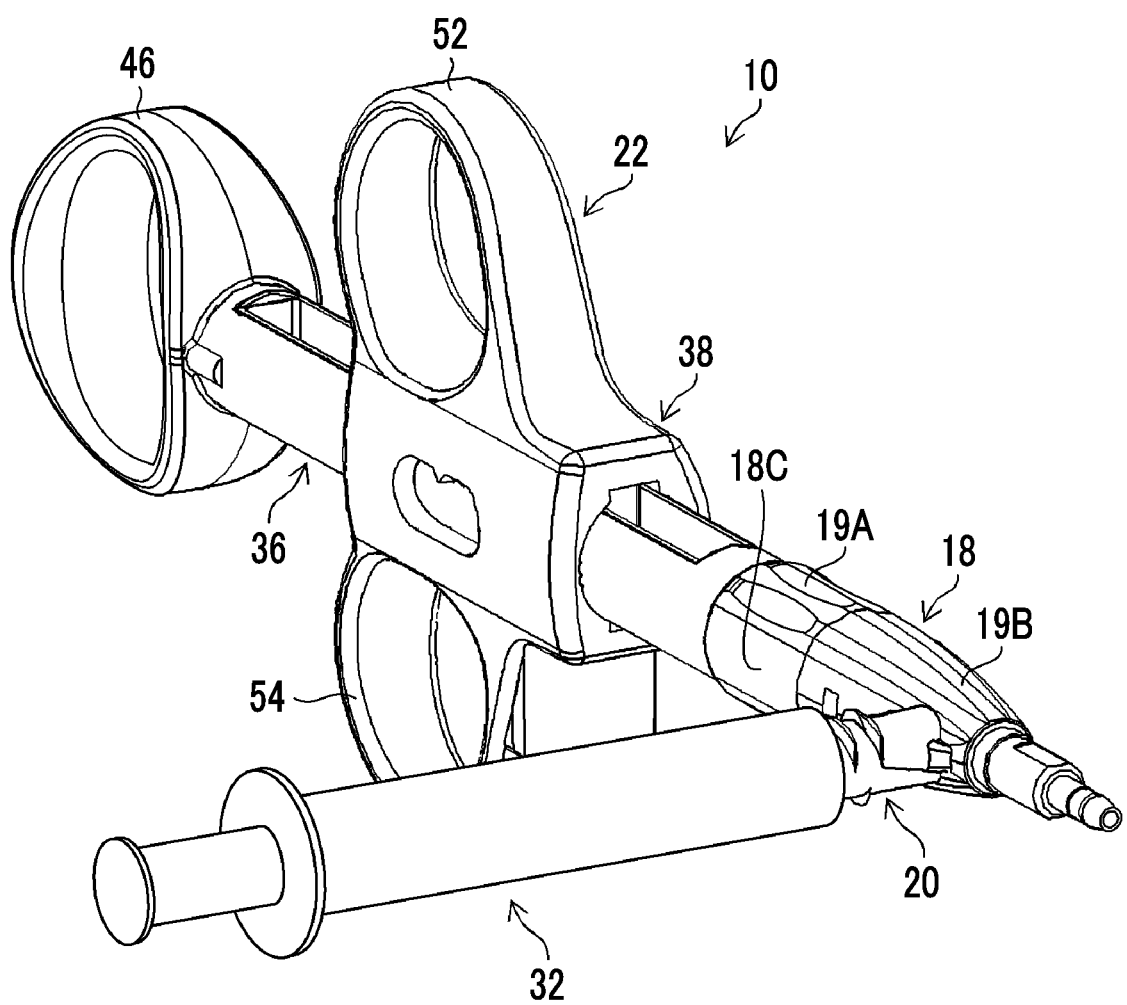
FIG. 7 is a perspective view of a high-frequency treatment tool with a syringe connected to a water injection connector.
Figure 8:
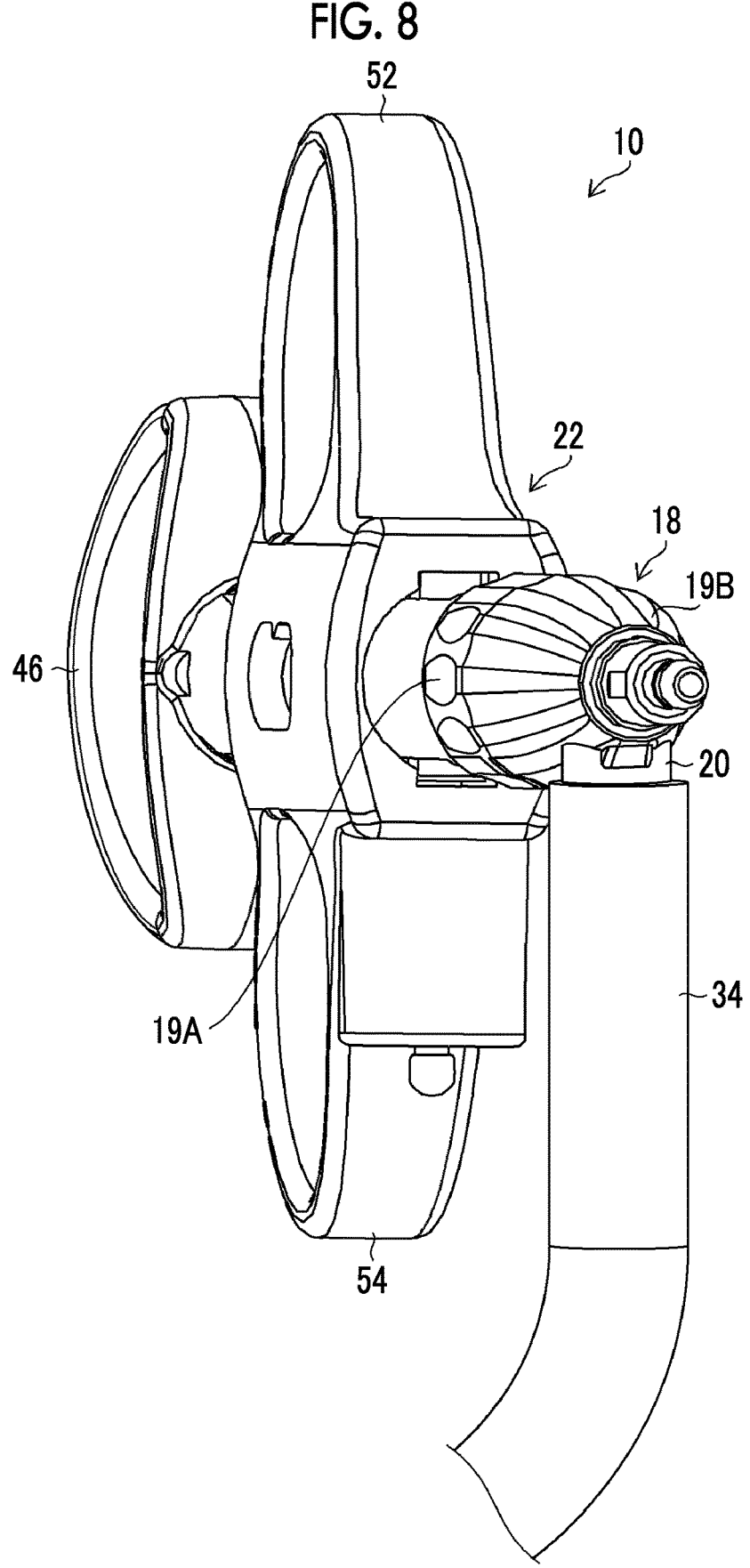
FIG. 8 is a perspective view of the high-frequency treatment tool with a water supply tube connected to the water injection connector.

Any one of the syringe 32 shown in FIG. 7 or the water supply tube 34 shown in FIG. 8 is selected to be connected to the water injection connector 20, for example. In a case where liquid such as an isotonic sodium chloride solution is supplied to the water injection path 21 of the water injection connector 20 from the syringe 32 or the water supply tube 34, the liquid is supplied into the sheath 12 (refer to FIG. 1) through the internal space 24 of the water injection connector 20 shown in FIG. 6 and is ejected to the outside from a distal end 26 of the sheath 12 thereafter. The water injection connector 20 will be described later.

Referring again to FIG. 4, the operation part body 22 includes a body shaft portion 36, a slider 38, and an electrical connector 40. Note that, in FIG. 4, the slider 38 is denoted by a two-dot chain line.

The body shaft portion 36 is a member having a shaft shape extending along the rotation axis 28. The body shaft portion 36 has a longitudinal axis 36A on the same axis as the rotation axis 28. In addition, at a distal end of the body shaft portion 36, a connection tube 42 is provided on the same axis as the longitudinal axis 36A. A water-stopping O-ring 44 is mounted onto the connection tube 42 and the connector body 18 is rotatably connected to the connection tube 42 via the O-ring 44.

Specifically, the connection tube 42 is configured to have a smaller diameter than the diameter of the body shaft portion 36. The connector body 18 is rotatably connected to the connection tube 42 while securing water-tightness with the connection tube 42 fitted into an opening 18A of a base portion of the connector body 18 via the O-ring 44.

In addition, a proximal end of the body shaft portion 36 is provided with a finger hook ring 46 into which a thumb of the operator is inserted. Furthermore, a slit 48 is formed in the body shaft portion 36. The slit 48 is formed along the longitudinal axis 36A.

Meanwhile, the slider 38 includes a tubular portion 50 into which the body shaft portion 36 is inserted and finger hook rings 52 and 54 into which an index finger and a middle finger of the operator are inserted. The finger hook rings 52 and 54 are integrally provided with side surfaces of the tubular portion 50 with the tubular portion 50 interposed therebetween.

Inside the tubular portion 50, the core 56 fixed to the tubular portion 50 is provided. The core 56 is slidably fitted and mounted into the slit 48 in a state where the rotation thereof around the longitudinal axis 36A is restricted. Therefore, the slider 38 is mounted onto the body shaft portion 36 such that the slider 38 can reciprocate along the longitudinal axis 36A in a state where the rotation thereof around the longitudinal axis 36A is restricted due to a rotation restricting effect caused by the slit 48 and the core 56.

The core 56 is provided with the electrical connector 40. The electrical connector 40 is electrically connected to the proximal end of the wire 14 inside the core 56. The electrical connector 40 is connected to a high-frequency power source (not shown) via a cable in the case of ESD treatment.

According to the high-frequency treatment tool 10 configured as described above, the index finger and the middle finger of the operator are inserted into the finger hook rings 52 and 54 and the thumb is inserted into the finger hook ring 46. Thereafter, in a case where the index finger and the middle finger are moved in a direction toward the thumb and a direction away from the thumb, the slider 38 reciprocates along the longitudinal axis 36A. Accordingly, the wire 14 is moved forward and backward in an axial direction of the sheath 12 and thus the high-frequency knife 16 can be caused to project and retract from the distal end 26 of the sheath 12. In addition, in the case of ESD treatment, a high-frequency electric current from the high-frequency power source is caused to flow to the high-frequency knife 16 via the wire 14 from the electrical connector 40. Accordingly, it is possible to excise a lesioned mucous membrane by means of the high-frequency knife 16.

Meanwhile, the high-frequency treatment tool 10 in the first embodiment has the following configuration so that the usability thereof is made favorable regardless of which of the syringe 32 (refer to FIG. 7) and the water supply tube 34 (refer to FIG. 8) is connected to the water injection connector 20.

That is, as shown in FIG. 4, a rotation stopper 60 provided at the operation part body 22 and an abutting surface 62 (refer to FIGS. 5 and 6) provided at the connector body 18 are provided and the connector body 18 can transition between a rotation restricted state (for example, state shown in FIG. 7), in which the abutting surface 62 abuts the rotation stopper 60 such that rotation of the connector body 18 in one direction is restricted, and a rotation allowed state (for example, state shown in FIG. 8), in which the abutting surface 62 abutting the rotation stopper 60 is separated from the rotation stopper 60 and rotation of the connector body 18 in both directions is allowed, by rotating around the rotation axis 28 with respect to the operation part body 22. Hereinafter, a specific configuration for enabling the transition between the rotation restricted state and the rotation allowed state.

Figure 9:
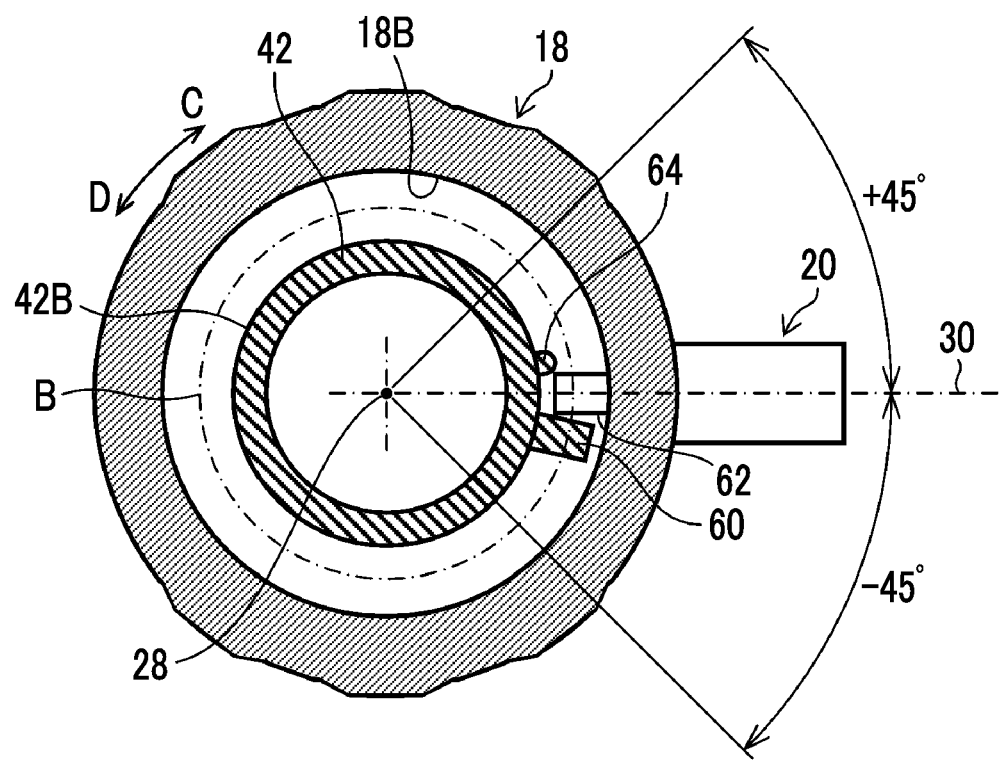
FIG. 9 is a sectional view taken along line 9-9 in FIG. 3.

FIG. 9 is a sectional view taken along line 9-9 in FIG. 3 and is an explanatory view showing a positional relationship among the connector body 18, the water injection connector 20, and the connection tube 42 as seen in a direction along an arrow A in FIG. 3. In addition, a state shown in FIG. 9 is a state shown in FIG. 7, which is an example of the rotation restricted state.

As shown in FIG. 9, the abutting surface 62 is formed at an inner peripheral surface 18B of the connector body 18. The abutting surface 62 is composed of a projecting portion protruding toward an outer peripheral surface 42B from the inner peripheral surface 18B. In addition, the rotation stopper 60 that restricts rotation of the connector body 18 is provided to protrude from the outer peripheral surface 42B of the connection tube 42 that faces the inner peripheral surface 18B. The rotation stopper 60 is composed of a projecting portion protruding toward the inner peripheral surface 18B from the outer peripheral surface 42B. The rotation stopper 60 is provided at a position overlapping a portion of a rotation trajectory B of the abutting surface 62, which is denoted by an one-dot chain line, as seen in a direction along the rotation axis 28. Note that, although the abutting surface 62 shown in FIG. 9 is composed of the projecting portion protruding toward the outer peripheral surface 42B from the inner peripheral surface 18B, the configuration thereof is not limited thereto as long as the abutting surface 62 is a surface that can abut the rotation stopper 60.

Here, the inner peripheral surface 18B is an example of a first peripheral surface according to the embodiment of the present invention and the outer peripheral surface 42B is an example of a second peripheral surface according to the embodiment of the present invention. In addition, in the embodiment, a configuration in which the connection tube 42 is inserted into the opening 18A of the connector body 18 is adopted. However, a configuration in which the base portion of the connector body 18 is inserted into an opening of the connection tube 42 may also be adopted. That is, the rotation stopper 60 may be provided on an inner peripheral surface of the opening of the connection tube 42 and the abutting surface 62 may be provided on an outer peripheral surface of the base portion of the connector body 18. In the case of such a configuration, the outer peripheral surface of the base portion of the connector body 18 is the first peripheral surface according to the embodiment of the present invention and the inner peripheral surface of the opening of the connection tube 42 is the second peripheral surface according to the embodiment of the present invention.

According to the high-frequency treatment tool 10 of the first embodiment, the rotation stopper 60 and the abutting surface 62 are provided and the abutting surface 62 abuts the rotation stopper 60 in a case where the connector body 18 rotates with respect to the operation part body 22 in the one direction denoted by an arrow C. Accordingly, the connector body 18 enters the rotation restricted state shown in FIG. 7 in which rotation thereof in the one direction is restricted. Note that, in the rotation restricted state shown in FIG. 7, the central axis 30 of the water injection connector 20 extends in a horizontal direction orthogonal to the rotation axis 28 with the high-frequency treatment tool 10 being in a posture (hereinafter, will be referred to as basic operation posture) in which the rotation axis 28 extends a horizontal direction and the finger hook rings 52 and 54 extend in a vertical direction.

In a case where the syringe 32 is to be used by being connected to the water injection connector 20, a transition to the rotation restricted state (that is, state where abutting surface 62 abuts rotation stopper 60) is made such that the syringe 32 connected to the water injection connector 20 is maintained in the rotation restricted state due to the weight thereof. Accordingly, the syringe 32 does not rotate together with the connector body 18 and thus there is an improvement in operability of the high-frequency treatment tool 10. In addition, in a case where the syringe 32 is to be connected to the water injection connector 20 as well, a transition to the rotation restricted state is made such that the syringe 32 can be easily connected to the water injection connector 20. Therefore, according to the high-frequency treatment tool 10 in the first embodiment, the usability thereof is favorable in a case where the syringe 32 is used by being connected.

Meanwhile, in a case where the connector body 18 is rotated in a direction denoted by an arrow D in the rotation restricted state shown in FIG. 9, the abutting surface 62 is positioned at a position separated from a position where the abutting surface 62 abuts the rotation stopper 60. In this case, the connector body 18 enters the rotation allowed state where rotation thereof in both directions is allowed.

In a case where the water supply tube 34 (refer to FIG. 8) is to be used by being connected to the water injection connector 20, a transition to the rotation allowed state (that is, state where abutting surface 62 is separated from position where abutting surface 62 abuts rotation stopper 60) is made. Specifically, the connector body 18 in the rotation restricted state as shown in FIG. 9 is rotated in the direction along the arrow D such that the connector body 18 is disposed at a position at which the water injection connector 20 faces a lower side in the vertical direction (that is, position at which central axis 30 of water injection connector 20 extends straight downward). In the rotation allowed state, even in a case where there is a change in positional relationship between the high-frequency treatment tool 10 and the water supply tube 34, the change can be absorbed by means of rotation of the connector body 18. Accordingly, the operability of the high-frequency treatment tool 10 is made favorable.

As described above, according to the high-frequency treatment tool 10 in the first embodiment, the connector body 18 is connected to the operation part body 22 such that the connector body 18 can rotate around the rotation axis 28, the rotation stopper 60 provided at the operation part body 22 and the abutting surface 62 provided at the connector body 18 are provided, and the connector body 18 can transition between the rotation restricted state, in which the abutting surface 62 abuts the rotation stopper 60 such that rotation of the connector body 18 in the one direction is restricted, and a rotation allowed state, in which the abutting surface 62 abutting the rotation stopper 60 is released and rotation of the connector body 18 in both directions is allowed, by rotating around the rotation axis 28 with respect to the operation part body 22. Therefore, the usability thereof is favorable regardless of which of the syringe 32 and the water supply tube 34 is used by being connected to the water injection connector 20.

Note that, in the above-described first embodiment, the rotation stopper 60 is provided at such a position that the central axis 30 of the water injection connector 20 extends in the horizontal direction in a case where the high-frequency treatment tool 10 is in the basic operation posture as shown in FIG. 7. However, the position of the rotation stopper 60 is not limited to the above-described position. That is, the position of the rotation stopper 60 may be within an area that does not impair the usability regardless of which of the syringe 32 and the water supply tube 34 is connected to the water injection connector 20. Specifically, it is preferable that the rotation stopper 60 is preferably provided at a position at which a difference between a reference angle and the rotation angle of the connector body 18 in a case where the abutting surface 62 abuts the rotation stopper 60 and rotation of the connector body 18 in the one direction is restricted is within ±45 degrees. Note that, the reference angle is the rotation angle of the connector body in a case where the central axis 30 of the water injection connector 20 extends in a second direction, which is one of horizontal directions orthogonal to a first direction, with the rotation axis 28 disposed to be parallel to the first direction, which is one of horizontal directions, as shown in FIG. 9. In a case where the rotation stopper 60 is provided within such an area, the usability is favorable regardless of which of the syringe 32 and the water supply tube 34 is used by being connected to the water injection connector 20.

In addition, in the case of the high-frequency treatment tool 10 in the first embodiment, as shown in FIG. 9, a sliding contact surface 64 is preferably provided on the outer peripheral surface 42B of the connection tube 42 and the connector body 18 is preferably configured to rotate while abutting the sliding contact surface 64. Note that, although the sliding contact surface 64 shown in FIG. 9 is composed of a projecting portion protruding toward the inner peripheral surface 18B from the outer peripheral surface 42B, the configuration thereof is not limited thereto as long as the sliding contact surface 64 is a surface that can abut the connector body 18.

The sliding contact surface 64 is provided at a position that is close to an abutting position, at which the abutting surface 62 abuts the rotation stopper 60, and is provided upstream of the abutting position in one rotation direction of the connector body 18 which is denoted by the arrow C. In a case where the sliding contact surface 64 is provided, frictional resistance is generated by the abutting surface 62 coming into sliding contact with the sliding contact surface 64 in the case of rotation of the connector body 18 in the one direction represented by the arrow C. By means of the frictional resistance, it is possible to apply an appropriate load to a rotation operation of the connector body 18. In addition, after the abutting surface 62 passes by the sliding contact surface 64, the abutting surface 62 abuts the rotation stopper 60 and thus the connector body 18 enters the rotation restricted state. Since such a sliding contact surface 64 is provided, it is possible to reliably make the operator feel that the abutting surface 62 has abutted the rotation stopper 60 by means of a load that is generated in a case where the abutting surface 62 passes by the sliding contact surface 64 and the feeling of locking caused by the abutting surface 62 abutting the rotation stopper 60. In addition, since the connector body 18 does not rotate in the direction along the arrow D to an opposite side in a case where a rotational force exceeding the above-described frictional resistance is not applied to the connector body 18 in the rotation restricted state, it is possible to prevent the connector body 18 from being accidentally rotated in the direction along the arrow D. Hereinabove, a configuration the sliding contact surface 64 is provided at the outer peripheral surface 42B of the connection tube 42 has been described. However, the sliding contact surface 64 may not be provided.

Figure 10:
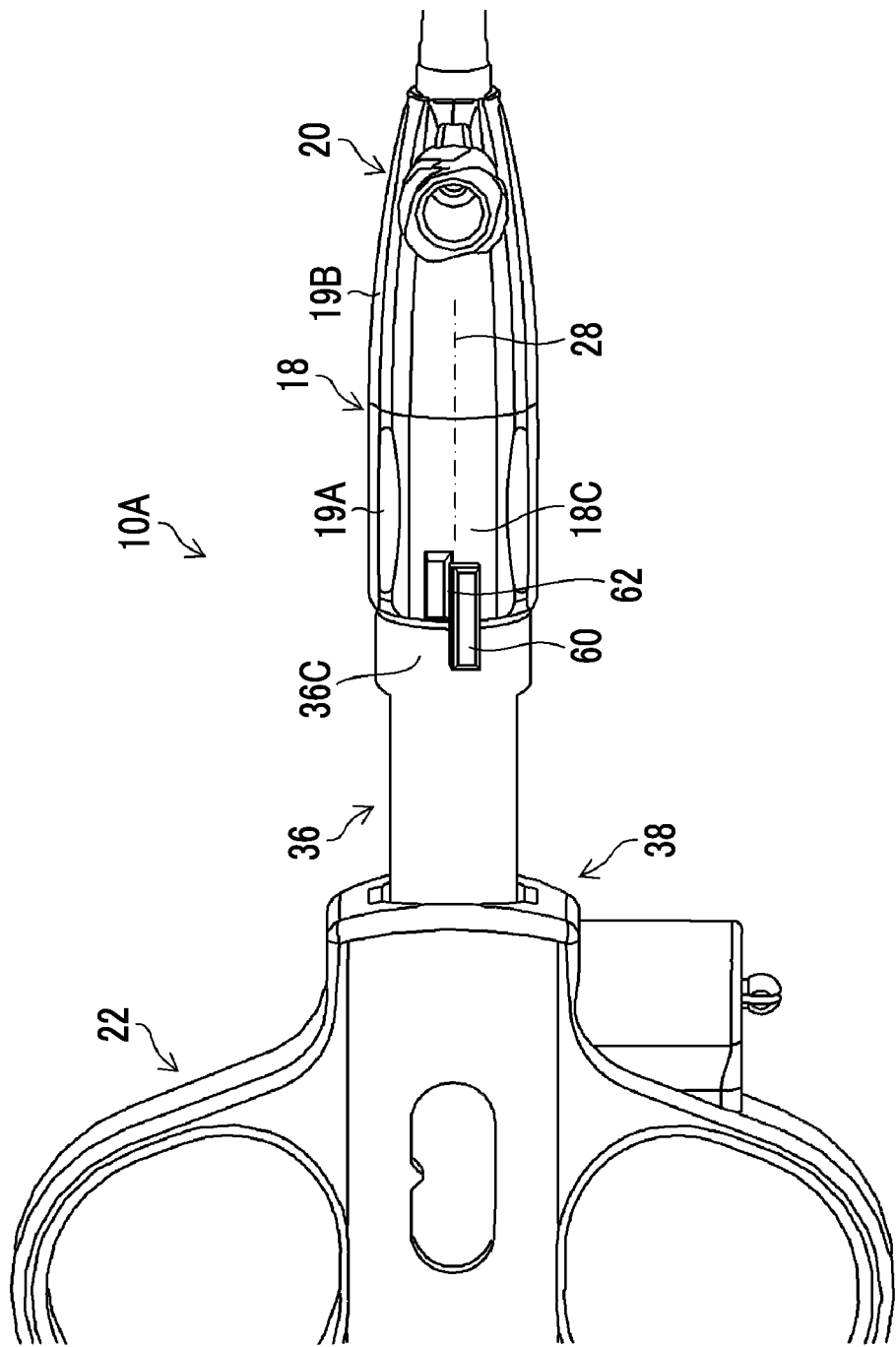
FIG. 10 is a main part plan view showing a high-frequency treatment tool in which the disposition positions of a rotation stopper and an abutting surface are changed.

FIG. 10 is a main part plan view showing a high-frequency treatment tool 10A in a second embodiment and shows a modification example of the disposition positions of the rotation stopper and the abutting surface according to the embodiment of the present invention. Note that, in the description of the high-frequency treatment tool 10A, the same or similar members as the high-frequency treatment tool 10 shown in FIGS. 1 to 9 will be given the same reference numerals and the description thereof will be omitted. In addition, the same applies to high-frequency treatment tools 10B to 1° F. in the second embodiment to a seventh embodiment which will be described below.

According to the high-frequency treatment tool 10A shown in FIG. 10, the abutting surface 62 is provided on the outer peripheral surface 18C of the connector body 18 and the rotation stopper 60 is provided on an outer peripheral surface 36C of the body shaft portion 36. The rotation stopper 60 is provided to extend toward the connector body 18 from the body shaft portion 36 and is disposed to be brought into sliding contact with the outer peripheral surface 18C of the connector body 18 or be separated from the outer peripheral surface 18C. According to the rotation stopper 60 and the abutting surface 62 configured as described above, in a case where the connector body 18 is rotated in the one direction, the abutting surface 62 abuts the rotation stopper 60 and the connector body 18 can enter the rotation restricted state.

In a case where the abutting surface 62 is provided on the outer peripheral surface 18C and the rotation stopper 60 is provided on the outer peripheral surface 36C as shown in FIG. 10, it is possible to visually recognize the relative positions of the rotation stopper 60 and the abutting surface 62 from the outside of the high-frequency treatment tool 10. Accordingly, the operator can easily check whether the connector body 18 is in the rotation restricted state or the connector body 18 is the rotation allowed state. Note that, in the embodiment shown in FIG. 10, the outer peripheral surface 18C corresponds to the first peripheral surface according to the embodiment of the present invention and the outer peripheral surface 36C corresponds to the second peripheral surface according to the embodiment of the present invention.

Figure 11:
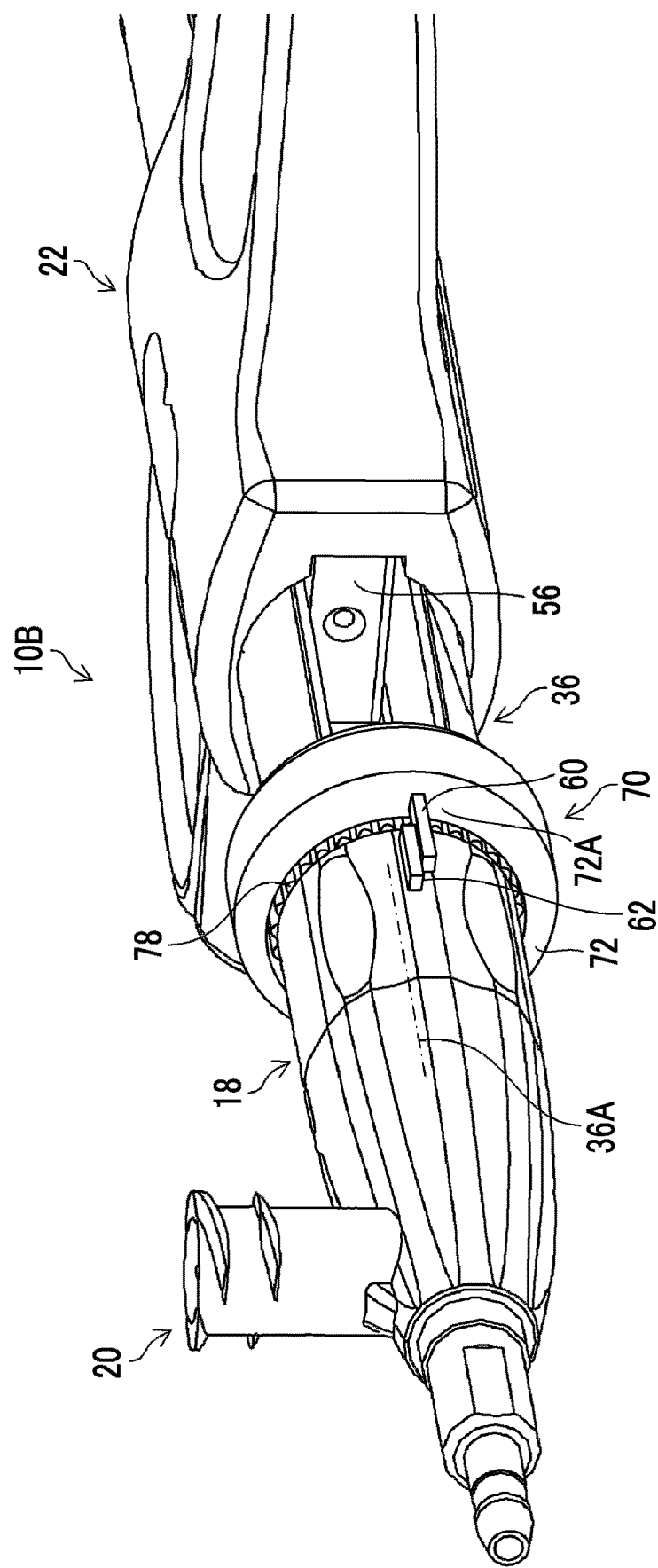
FIG. 11 is an explanatory view of a configuration in which the position of the rotation stopper of an operation part body can be changed.
Figure 12:
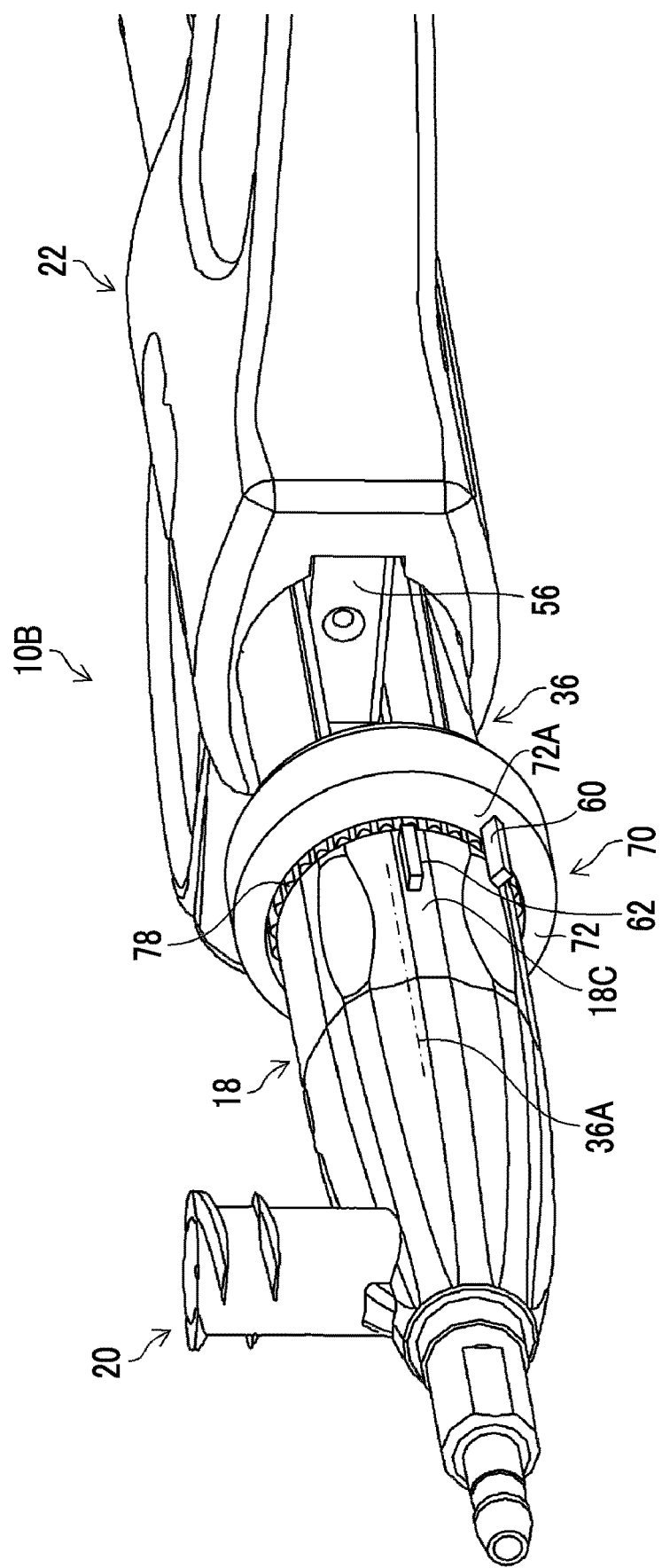
FIG. 12 is an explanatory view in which the position of the rotation stopper in a circumferential direction around a rotation axis is changed.
Figure 13:
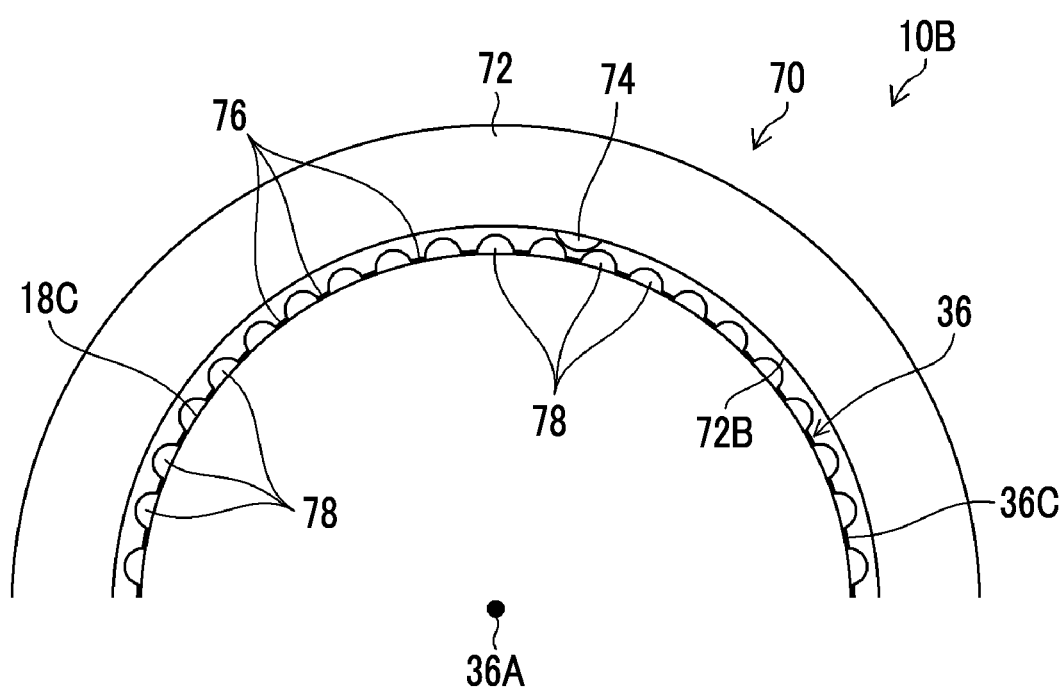
FIG. 13 is an explanatory view showing an example of a position change mechanism of the rotation stopper.

FIGS. 11 to 13 are explanatory views of a high-frequency treatment tool 10B according to the third embodiment and show an example of a position change mechanism 70 with which it is possible to change the position of the rotation stopper 60 of the operation part body 22. That is, FIG. 11 shows the rotation restricted state in which the abutting surface 62 abuts the rotation stopper 60 before a position change. FIG. 12 shows a state where the position of the rotation stopper 60 is changed from the position shown in FIG. 11 by means of the position change mechanism 70. FIG. 13 shows an example of the position change mechanism 70 and is a main part enlarged view of the position change mechanism 70. Note that, the abutting surface 62 is provided on the outer peripheral surface 18C of the connector body 18 as with the high-frequency treatment tool 10A shown in FIG. 10.

As shown in FIG. 13, the position change mechanism 70 includes a position change ring 72, an engaging protrusion 74, and a plurality of engaging recess portions 76.

The position change ring 72 is provided at a distal end of the body shaft portion 36 such that the position change ring 72 can rotate around the longitudinal axis 36A. As shown in FIG. 11, on a side surface 72A of the position change ring 72 that is on the distal end side, the rotation stopper 60 is provided to extend along the longitudinal axis 36A. As shown in FIG. 13, the engaging protrusion 74 is provided on an inner peripheral surface 72B of the position change ring 72. In addition, the plurality of engaging recess portions 76 are formed between projecting portions 78 and 78 adjacent to each other with a plurality of the projecting portions 78,78 and . . . formed on the outer peripheral surface 36C of the body shaft portion 36 at intervals in a circumferential direction around the longitudinal axis 36A.

According to the position change mechanism 70 configured as described above, in a case where the position change ring 72 is rotated around the longitudinal axis 36A, the engaging protrusion 74 sequentially engages with the engaging recess portions 76, 76 and . . . while climbing over the projecting portions 78. Accordingly, the position change ring 72 is rotated with respect to the body shaft portion 36 with a frictional force and the position of the rotation stopper 60 can be changed to any position with the engaging protrusion 74 engaging with the engaging recess portion 76. Accordingly, the rotation stopper 60 is configured such that the position of the rotation stopper 60 in a circumferential direction around the rotation axis 28 in the operation part body 22 can be changed by means of the position change mechanism 70. With such a position change mechanism 70, it is possible to change the position of the rotation stopper 60 to any position.

Note that, although the position change mechanism 70 as shown in FIGS. 11 to 13 has been described as an example of a unit that changes the position of the rotation stopper 60 to any position, the unit is not limited to the position change mechanism 70. For example, a configuration in which a plurality of engaging portions are provided on the outer peripheral surface 36C of the body shaft portion 36 in the circumferential direction around the rotation axis 28 and one of the engaging portions attachably and detachably engages with the rotation stopper 60 may also be adopted. Even in the case of such a configuration, it is possible to achieve the same effect as the position change mechanism 70. Note that, examples of the above-described engaging portion include an engaging hole.

Meanwhile, in a case where the syringe 32 is used by being connected to the water injection connector 20 in the rotation restricted state shown in FIG. 7, the operator needs to operate the high-frequency treatment tool 10 while paying attention to the posture such as the inclination and the orientation of the high-frequency treatment tool 10 such that the syringe 32 does not rotate together with the connector body 18, that is, within such a range that the rotation restricted state is maintained due to the weight of the syringe 32.

Figure 14:
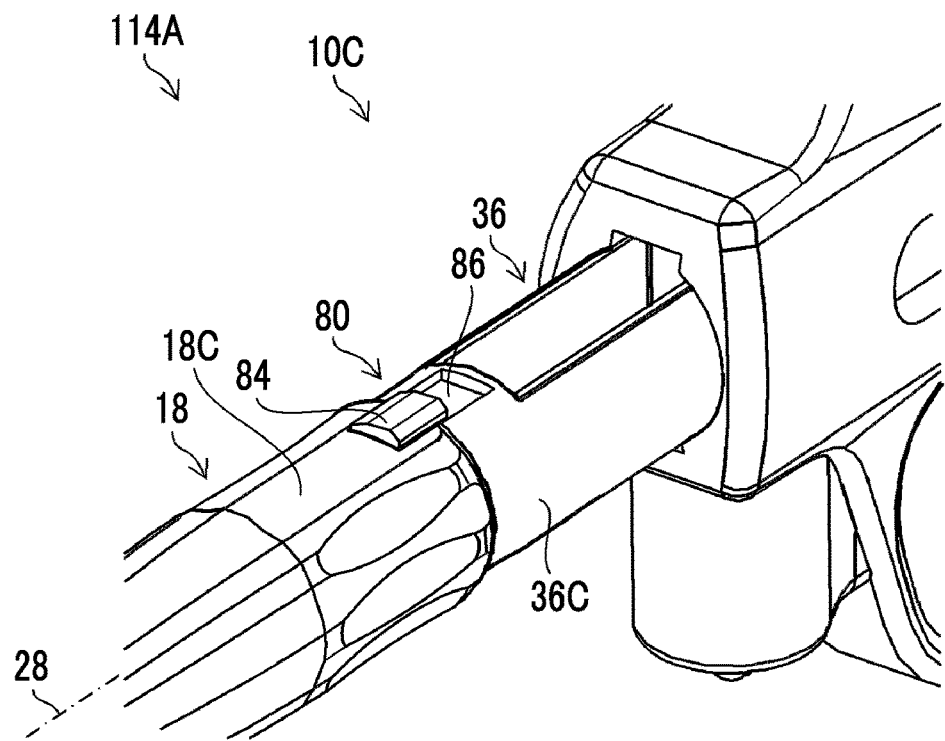
FIG. 14 is a main part configuration view showing a high-frequency treatment tool in which a connector body can be switched between a rotation locked state and a rotation unlocked state by means of a sliding type lock switch.
Figure 14:
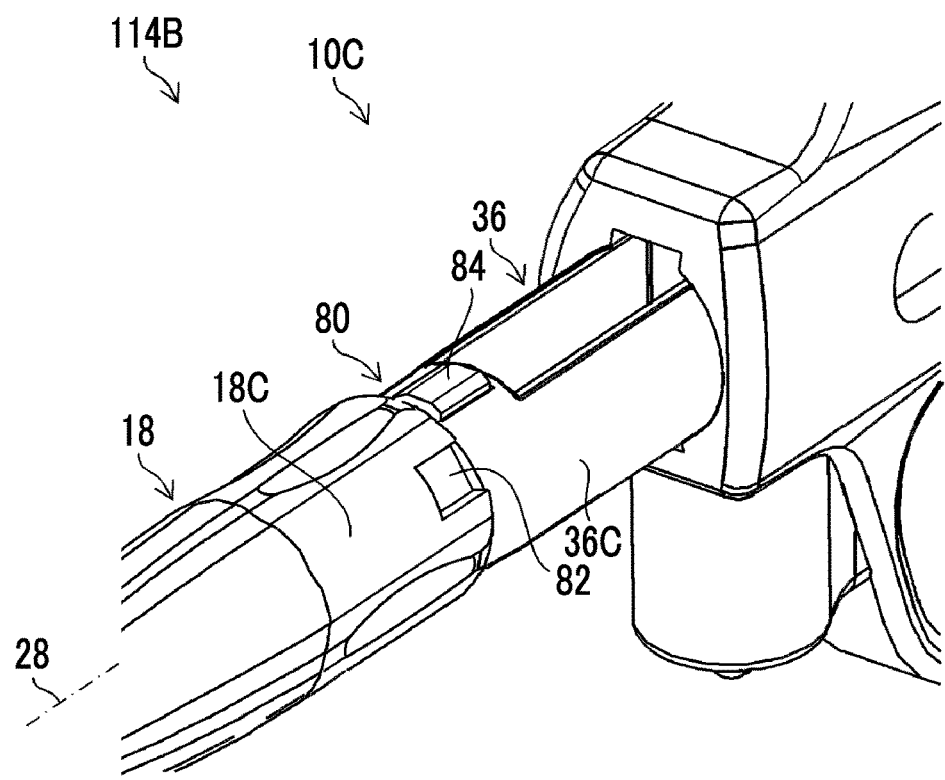

FIG. 14 is a main part perspective view showing a high-frequency treatment tool 10C according to a fourth embodiment. The high-frequency treatment tool 10C includes a sliding type lock switch 80 that switches the rotation of the connector body 18 between a rotation locked state and a rotation unlocked state such that the above-described problem is solved.

As shown in 114A and 114B of FIG. 14, the lock switch 80 includes an engaged portion 82 provided on the connector body 18 and a movable engaging body 84 provided on the body shaft portion 36.

The engaged portion 82 is composed of a groove portion having a recess shape provided on the outer peripheral surface 18C of the connector body 18. The movable engaging body 84 constitutes a slide switch that can slide along an axial direction along the rotation axis 28 with respect to a guide groove 86 formed on the outer peripheral surface 36C of the body shaft portion 36.

In a case where the movable engaging body 84 is slid toward the engaged portion 82, the movable engaging body 84 engages with the engaged portion 82 (refer to 114B of FIG. 14) as shown in 114A of FIG. 14. Accordingly, the connector body 18 enters the rotation locked state in which the connector body 18 is locked by the movable engaging body 84 with the connector body 18 being not rotatable. In addition, in a case where the movable engaging body 84 is slid in a direction away from the engaged portion 82, the movable engaging body 84 is disengaged from the engaged portion 82 as shown in 114B of FIG. 14. Accordingly, the connector body 18 enters the rotation unlocked state. That is, the movable engaging body 84 is configured to rotate between the rotation locked state and the rotation unlocked state. Note that, the movable engaging body 84 engages with the engaged portion 82 at a position in the rotation restricted state shown in FIG. 7.

According to the high-frequency treatment tool 10C in the fourth embodiment, since the lock switch 80 as described above is provided, effects as follows can be achieved. For example, in a case where the syringe 32 is to be used by being connected to the water injection connector 20, after the connector body 18 is rotated to a position at which the movable engaging body 84 engages with the engaged portion 82 (that is, position at which engaged portion 82 faces movable engaging body 84), the movable engaging body 84 is slid to engage with the engaged portion 82 such that the connector body 18 enters the rotation locked state. Accordingly, the operator can concentrate on the operation of the high-frequency treatment tool 10C without particularly paying attention to the posture such as the inclination or the orientation of the high-frequency treatment tool 10C. In addition, in a case where the water supply tube 34 in FIG. 8 is to be used by being connected to the water injection connector 20, the movable engaging body 84 is moved to retract from the engaged portion 82 such that the rotation unlocked state is achieved. Accordingly, as with the high-frequency treatment tool 10 according to the first embodiment, the usability is favorable even in a case where the water supply tube 34 is used by being connected.

Figure 15:
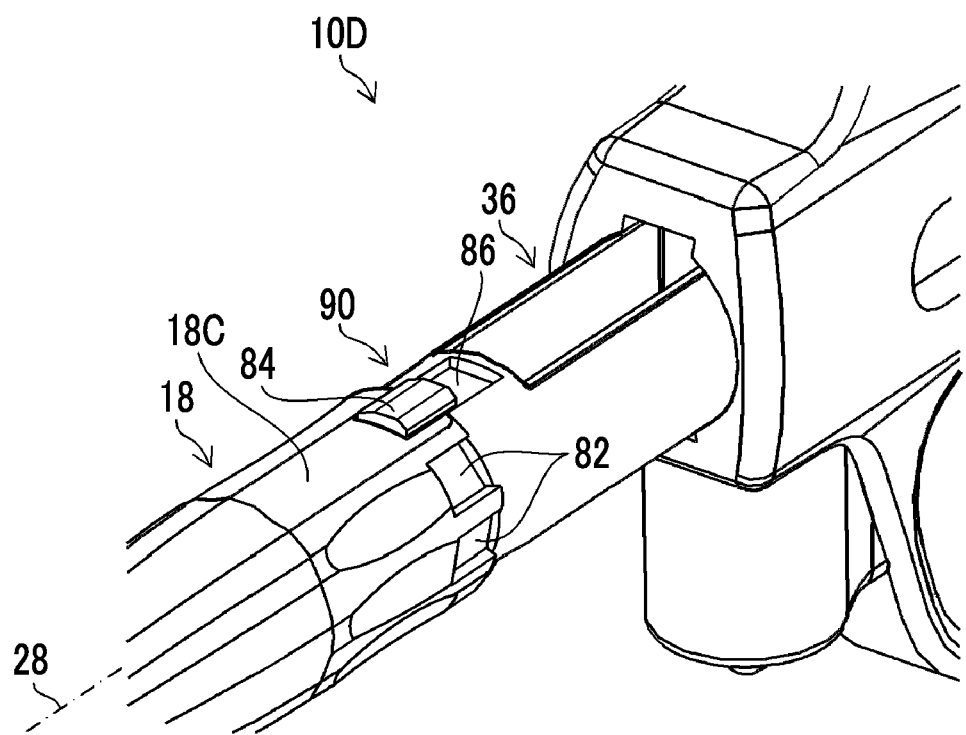
FIG. 15 is a main part configuration view showing a modification example of the lock switch in FIG. 14.

FIG. 15 is a main part perspective view showing a high-frequency treatment tool 10D according to a fifth embodiment. A lock switch 90 shown in FIG. 15 includes a plurality of engaged portions 82, 82 and . . . provided on the outer peripheral surface 18C of the connector body 18 in a circumferential direction around the rotation axis 28 and other configurations thereof are the same as those of the lock switch 80 in FIG. 14. According to the lock switch 90 shown in FIG. 15, it is possible to select the engaged portion 82 engaging with the movable engaging body 84 from among the plurality of engaged portions 82, 82 and . . . . Therefore, it is possible to change the orientation of the water injection connector 20 to a desired position in the case of the rotation restricted state.

Figure 16:
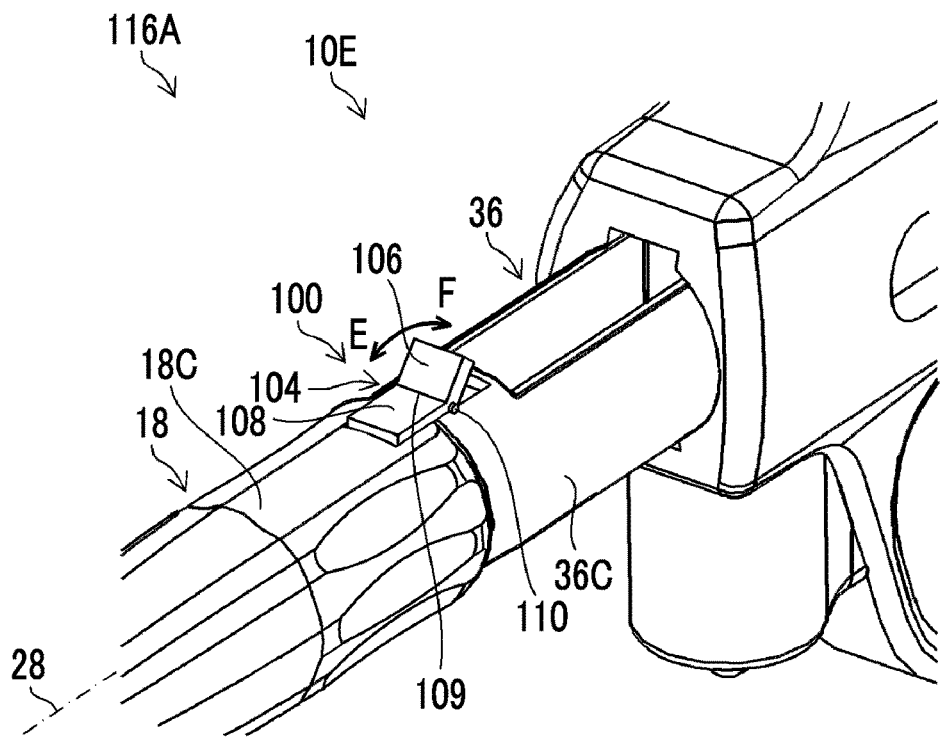
FIG. 16 is a main part configuration view showing a high-frequency treatment tool in which a connector body can be switched between the rotation locked state and the rotation unlocked state by means of a rocking type lock switch.
Figure 16:
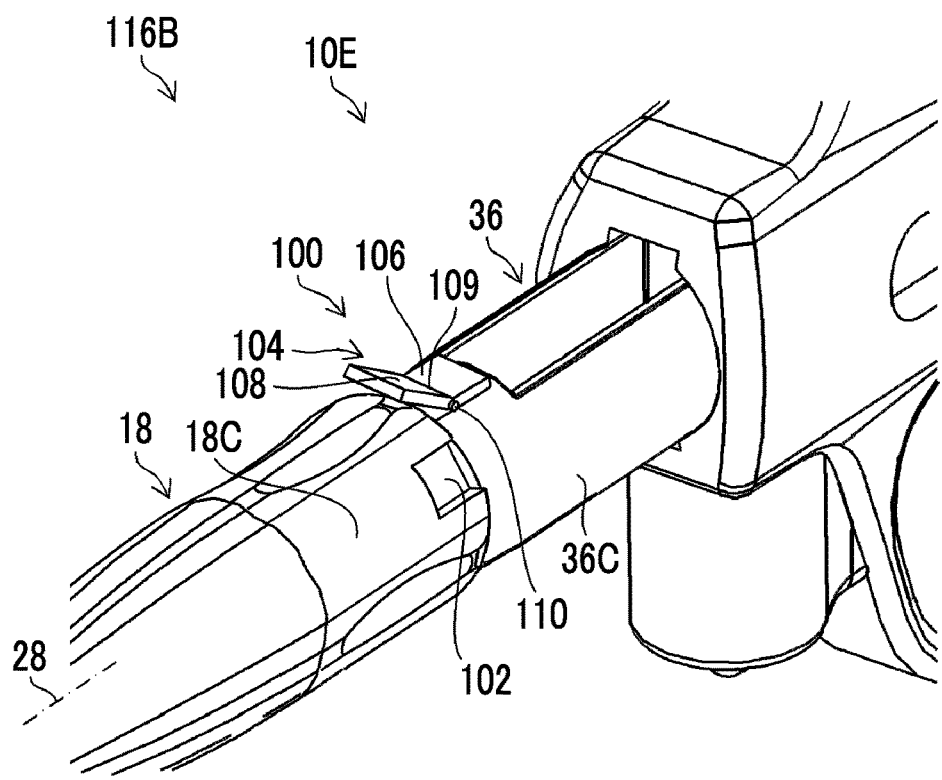

FIG. 16 is a main part perspective view showing a high-frequency treatment tool 10E according to a sixth embodiment. The high-frequency treatment tool 10E includes a rocking type lock switch 100 that switches the rotation of the connector body 18 between a rotation locked state and a rotation unlocked state.

As shown in 116A and 116B of FIG. 16, the lock switch 100 includes an engaged portion 102 provided on the connector body 18 and a movable engaging body 104 provided on the body shaft portion 36.

The engaged portion 102 is composed of a groove portion having a recess shape provided on the outer peripheral surface 18C of the connector body 18. The movable engaging body 104 constitutes a rocking switch and includes a rocking body 106 and an engaging portion 108 that can engage with the engaged portion 102. Each of the rocking body 106 and the engaging portion 108 is configured to have a plate shape and the rocking body 106 and the engaging portion 108 are configured to form a V-shape as seen from a lateral side, with a bearing portion 109 interposed therebetween. The bearing portion 109 is provided to be capable of rocking around a pin 110 provided on the outer peripheral surface 36C of the body shaft portion 36 and the pin 110 is attached in a direction orthogonal to a direction along the rotation axis 28.

According to the high-frequency treatment tool 10E in the sixth embodiment, since the lock switch 100 as described above is provided, effects as follows can be achieved. For example, in a case where the syringe 32 is to be used by being connected to the water injection connector 20, after the connector body 18 is rotated to a position at which the engaging portion 108 engages with the engaged portion 102 (that is, position at which engaged portion 102 faces engaging portion 108), the rocking body 106 is caused to rock in a direction along an arrow E such that the engaging portion 108 engages with the engaged portion 102 and the connector body 18 enters the rotation locked state. Accordingly, the operator can concentrate on the operation of the high-frequency treatment tool 10 without particularly paying attention to the posture such as the inclination or the orientation of the high-frequency treatment tool 10. In addition, in a case where the water supply tube 34 in FIG. 8 is to be used by being connected to the water injection connector 20, the rocking body 106 is caused to rock in a direction along an arrow F such that the engaging portion 108 is moved to retract from the engaged portion 102 and the rotation unlocked state is achieved. Accordingly, as with the high-frequency treatment tool 10 according to the first embodiment, the usability is favorable even in a case where the water supply tube 34 is used by being connected.

Figure 17:
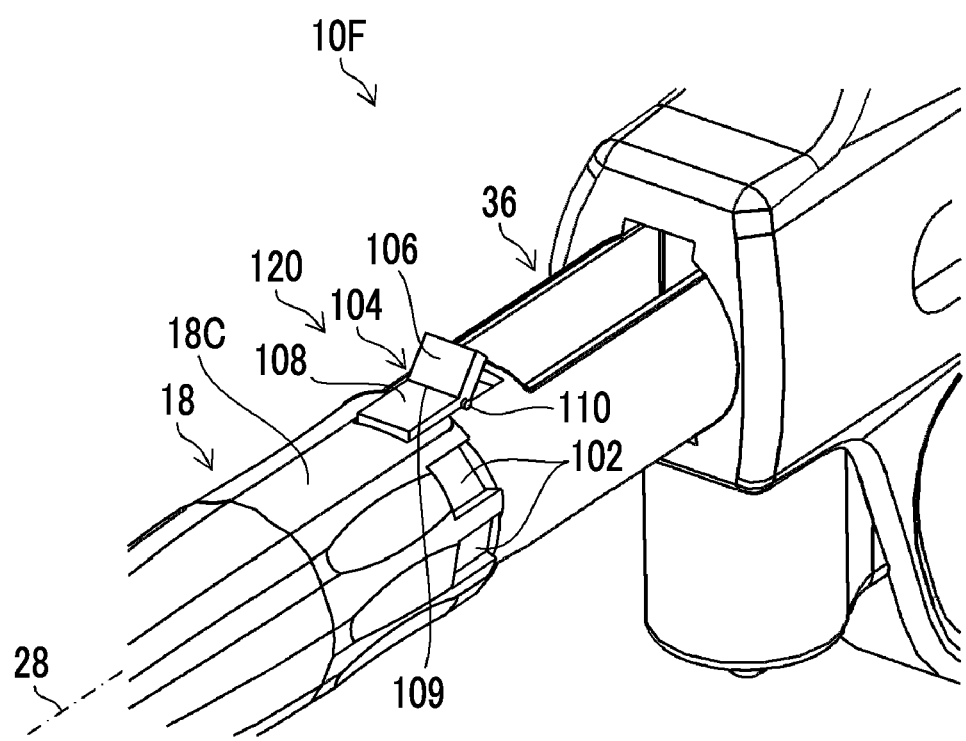
FIG. 17 is a main part configuration view showing a modification example of the lock switch in FIG. 16.

FIG. 17 is a main part perspective view showing a high-frequency treatment tool 10F according to a seventh embodiment. A lock switch 120 shown in FIG. 17 includes a plurality of engaged portions 102, 102 and . . . provided on the outer peripheral surface 18C of the connector body 18 in the circumferential direction around the rotation axis 28 and other configurations thereof are the same as those of the lock switch 100 in FIG. 16. According to the lock switch 120 shown in FIG. 17, it is possible to select the engaged portion 102 engaging with the engaging portion 108 from among the plurality of engaged portions 102, 102 and . . . . Therefore, it is possible to change the orientation of the water injection connector 20 to a desired position in the case of the rotation restricted state.

EXPLANATION OF REFERENCES

10: high-frequency treatment tool
10A: high-frequency treatment tool
10B: high-frequency treatment tool
10C: high-frequency treatment tool
10D: high-frequency treatment tool
10E: high-frequency treatment tool
10F: high-frequency treatment tool
12: sheath
14: wire
16: high-frequency knife
18: connector body
18A: opening
18B: inner peripheral surface
18C: outer peripheral surface
19A: finger hook portion
19B: slip prevention portion
20: water injection connector
21: water injection path
22: operation part body
24: internal space
26: distal end
28: rotation axis
30: central axis
32: syringe
34: water supply tube
36: body shaft portion
36A: longitudinal axis
36C: outer peripheral surface
38: slider
40: electrical connector
42: connection tube
42B: outer peripheral surface
44: O-ring
46: finger hook ring
48: slit
50: tubular portion
52: finger hook ring
54: finger hook ring
56: core
60: rotation stopper
62: abutting surface
64: sliding contact surface
70: position change mechanism
72: position change ring
74: engaging protrusion
76: engaging recess portion
78: projecting portion
80: lock switch 82: engaged portion
84: movable engaging body
86: guide groove
90: lock switch
100: lock switch
102: engaged portion
104: movable engaging body
106: rocking body
108: engaging portion
110: pin
120: lock switch

What is claimed is:

1. An endoscope treatment tool comprising:
a flexible sheath;
 a wire that is inserted into the sheath;
 a treatment unit that is provided at a distal end of the wire;
 a connector body having a tubular shape to which a proximal end of the sheath is connected;
 a water injection connector that is provided at the connector body; and
 an operation part body that is connected to a proximal end of the connector body and moves the wire forward and backward in an axial direction of the sheath such that the treatment unit projects and retracts from a distal end of the sheath,
wherein the connector body is connected to the operation part body such that the connector body is rotatable around a rotation axis,
the operation part body includes a rotation stopper and a sliding contact surface,
the connector body includes an abutting surface, and
the connector body is capable of transitioning between a rotation restricted state, in which the abutting surface abuts the rotation stopper such that a rotation direction of the connector body is restricted to be rotatable only in one direction, and a rotation allowed state, in which the abutting surface abutting the rotation stopper is released and rotation of the connector body in both directions is allowed, by rotating with respect to the operation part body, wherein a central axis of the water injection connector extends in a horizontal direction orthogonal to the rotation axis,
wherein the sliding contact surface and the rotation stopper restrict the abutting surface of the connector body in the rotation restricted state.

2. The endoscope treatment tool according to claim 1,
wherein, in a state where the rotation axis is disposed along a first direction which is one of horizontal directions, when it is assumed that a reference angle is a rotation angle of the connector body in a case where a central axis of the water injection connector is directed to a second direction which is one of the horizontal directions orthogonal to the first direction,
a difference between the reference angle and a rotation angle of the connector body is restricted is within 45 degrees, in a case where the abutting surface abuts on the rotation stopper such that the rotation direction of the connector body is restricted to be rotatable only in one direction.

3. The endoscope treatment tool according to claim 2,
wherein the central axis of the water injection connector is orthogonal to the rotation axis.

4. The endoscope treatment tool according to claim 2,
wherein the connector body includes an engaged portion, and
the operation part body includes a movable engaging body that is capable of operating between a rotation locked state in which the movable engaging body engages with the engaged portion and the connector body is locked so that the connector body being not rotatable and a rotation unlocked state in which the movable engaging body is disengaged from the engaged portion so that the connector body rotatable.

5. The endoscope treatment tool according to claim 1,
wherein the connector body includes a first peripheral surface extending along a circumferential direction around the rotation axis,
the operation part body includes a second peripheral surface extending along the circumferential direction around the rotation axis, and
the abutting surface is provided on the first peripheral surface and the rotation stopper is provided on the second peripheral surface.

6. The endoscope treatment tool according to claim 5,
wherein the second peripheral surface is provided with the sliding contact surface having a convex shape, and
the connector body is configured to rotate while abutting the sliding contact surface.

7. The endoscope treatment tool according to claim 1,
wherein the rotation stopper is configured such that a position of the rotation stopper in a circumferential direction around the rotation axis in the operation part body is changeable.

8. The endoscope treatment tool according to claim 1,
wherein the connector body includes an engaged portion, and
the operation part body includes a movable engaging body that is capable of operating between a rotation locked state in which the movable engaging body engages with the engaged portion and the connector body is locked so that the connector body being not rotatable and a rotation unlocked state in which the movable engaging body is disengaged from the engaged portion so that the connector body rotatable.

9. The endoscope treatment tool according to claim 8,
wherein the movable engaging body is a slide switch that is capable of sliding in an axial direction along the rotation axis.

10. The endoscope treatment tool according to claim 8,
wherein the movable engaging body is a rocking switch that is capable of rocking around a direction orthogonal to an axial direction along the rotation axis.

11. The endoscope treatment tool according to claim 1,
wherein the operation part body includes
 a body shaft portion to which the connector body is rotatably connected and that extends in a direction along the rotation axis,
 a slider that is provided to be movable along the body shaft portion and to which a proximal end portion of the wire is connected, and
 an electrical connector that is provided in the slider and is electrically connected to the proximal end portion of the wire, and
the operation part body is capable of energizing the treatment unit.

12. An endoscope treatment tool comprising:
a flexible sheath;
a wire that is inserted into the sheath;
a treatment unit that is provided at a distal end of the wire;
a connector body having a tubular shape to which a proximal end of the sheath is connected;

a water injection connector that is provided at the connector body; and
an operation part body that is connected to a proximal end of the connector body and moves the wire forward and backward in an axial direction of the sheath such that the treatment unit projects and retracts from a distal end of the sheath,
wherein the connector body is connected to the operation part body such that the connector body is rotatable around a rotation axis,
the operation part body includes a rotation stopper and a sliding contact surface, and the rotation stopper and the sliding contact surface are protrusions respectively protrudes at different locations of a peripheral surface of the operation part body,
the connector body includes an abutting surface, and
the rotation stopper and the sliding contact surface are protrusions provided at positions overlapping a portion of a rotation trajectory of the abutting surface as seen in a direction along the rotation axis and are configured such that a rotation direction of the connector body is restricted to be rotatable only in one direction, with the abutting surface abutting the rotation stopper, and the sliding contact surface and the rotation stopper restrict the abutting surface of the connector body in a rotation restricted state with respect to the connector body, wherein a central axis of the water injection connector extends in a horizontal direction orthogonal to the rotation axis.

13. The endoscope treatment tool according to claim 12, wherein, in a state where the rotation axis is disposed along a first direction which is one of horizontal directions, when it is assumed that a reference angle is a rotation angle of the connector body in a case where a central axis of the water injection connector is directed to a second direction which is one of the horizontal directions orthogonal to the first direction,
a difference between the reference angle and a rotation angle of the connector body is restricted is within 45 degrees, in a case where the abutting surface abuts on the rotation stopper such that the rotation direction of the connector body is restricted to be rotatable only in one direction.

14. The endoscope treatment tool according to claim 12, wherein the connector body includes a first peripheral surface extending along a circumferential direction around the rotation axis,
the operation part body includes a second peripheral surface extending along the circumferential direction around the rotation axis, and
the abutting surface is provided on the first peripheral surface and the rotation stopper is provided on the second peripheral surface.

15. The endoscope treatment tool according to claim 12, wherein the rotation stopper is configured such that a position of the rotation stopper in a circumferential direction around the rotation axis in the operation part body is changeable.

16. The endoscope treatment tool according to claim 12, wherein the connector body includes an engaged portion, and
the operation part body includes a movable engaging body that is capable of operating between a rotation locked state in which the movable engaging body engages with the engaged portion and the connector body is locked so that the connector body being not rotatable and a rotation unlocked state in which the movable engaging body is disengaged from the engaged portion so that the connector body rotatable.

17. An endoscope treatment tool comprising:
a flexible sheath;
a wire that is inserted into the sheath;
a treatment unit that is provided at a distal end of the wire;
a connector body having a tubular shape to which a proximal end of the sheath is connected;
a water injection connector that is provided at the connector body; and
an operation part body that is connected to a proximal end of the connector body and moves the wire forward and backward in an axial direction of the sheath such that the treatment unit projects and retracts from a distal end of the sheath,
wherein the connector body is connected to the operation part body such that the connector body is rotatable around a rotation axis,
the operation part body includes a rotation stopper,
the connector body includes an abutting surface, and
the connector body is capable of transitioning between a rotation restricted state, in which the abutting surface abuts the rotation stopper such that rotation of the connector body in one direction is restricted, and a rotation allowed state, in which the abutting surface abutting the rotation stopper is released and rotation of the connector body in both directions is allowed, by rotating with respect to the operation part body,
the connector body includes a first peripheral surface extending along a circumferential direction around the rotation axis,
the operation part body includes a second peripheral surface extending along the circumferential direction around the rotation axis,
the abutting surface is provided on the first peripheral surface and the rotation stopper is provided on the second peripheral surface,
the second peripheral surface is provided with a sliding contact surface having a convex shape, and
the connector body is configured to rotate while abutting the sliding contact surface, wherein a central axis of the water injection connector extends in a horizontal direction orthogonal to the rotation axis,
wherein the sliding contact surface and the rotation stopper restrict the abutting surface of the connector body in the rotation restricted state.

18. An endoscope treatment tool comprising:
a flexible sheath;
a wire that is inserted into the sheath;
a treatment unit that is provided at a distal end of the wire;
a connector body having a tubular shape to which a proximal end of the sheath is connected;
a water injection connector that is provided at the connector body; and
an operation part body that is connected to a proximal end of the connector body and moves the wire forward and backward in an axial direction of the sheath such that the treatment unit projects and retracts from a distal end of the sheath,
wherein the connector body is connected to the operation part body such that the connector body is rotatable around a rotation axis,
the operation part body includes a rotation stopper,
the connector body includes an abutting surface, the rotation stopper is provided at a position overlapping a portion of a rotation trajectory of the abutting surface as seen in a direction along the rotation axis and is configured to restrict rotation of the connector body in one direction with the abutting surface abutting the rotation stopper, the connector body includes a first peripheral surface extending along a circumferential direction around the rotation axis, the operation part body includes a second peripheral surface extending along the circumferential direction around the rotation axis, the abutting surface is provided on the first peripheral surface and the rotation stopper is provided on the second peripheral surface, the second peripheral surface is provided with a sliding contact surface having a convex shape, and the connector body is configured to rotate while abutting the sliding contact surface, wherein a central axis of the water injection connector extends in a horizontal direction orthogonal to the rotation axis, wherein the sliding contact surface and the rotation stopper restrict the abutting surface of the connector body in a rotation restricted state.

* * * * *